United States Patent [19]

Chari et al.

[11] Patent Number: 5,543,276

[45] Date of Patent: Aug. 6, 1996

[54] COLOR PHOTOGRAPHIC ELEMENT CONTAINING NEW EPOXY SCAVENGERS FOR RESIDUAL MAGENTA COUPLER

[75] Inventors: Krishnan Chari, Rochester; Wendell F. Smith, Jr.; Paul P. Spara, both of Fairport; Sundaram Krishnamurthy, Penfield, all of N.Y.

[73] Assignee: Eastman Kodak Company, Rochester, N.Y.

[21] Appl. No.: 255,512

[22] Filed: Jun. 8, 1994

[51] Int. Cl.$^6$ .............................. G03C 7/392; G03C 1/34
[52] U.S. Cl. .................... 430/505; 430/551; 430/554; 430/555; 430/558; 430/638
[58] Field of Search .................... 430/545, 546, 430/551, 554, 555, 558, 638, 505

[56] References Cited

U.S. PATENT DOCUMENTS

| | | | |
|---|---|---|---|
| 4,239,851 | 12/1980 | Aoki et al. | 430/546 |
| 4,540,657 | 9/1985 | Krishnamurthy | 430/546 |
| 4,745,052 | 5/1988 | Renner | 430/555 |
| 4,900,655 | 2/1990 | Nakazyo et al. | 430/546 |
| 5,001,045 | 3/1991 | Furutachi et al. | 430/545 |
| 5,047,315 | 9/1991 | Morigaki et al. | 430/544 |
| 5,183,731 | 2/1993 | Takahashi et al. | 430/551 |
| 5,200,307 | 4/1993 | Takahashi | 430/546 |
| 5,300,394 | 4/1994 | Miller et al. | 430/137 |

FOREIGN PATENT DOCUMENTS

| | | |
|---|---|---|
| 273412A3 | 7/1988 | European Pat. Off. |
| 0435179A2 | 12/1990 | European Pat. Off. |
| 0472153 | 2/1992 | European Pat. Off. |
| 0471347 | 2/1992 | European Pat. Off. |
| 0476604 | 3/1992 | European Pat. Off. |
| 2432041 | 1/1975 | Germany. |
| 51/003219 | 6/1974 | Japan. |
| 62/075449 | 9/1985 | Japan. |
| 62/080641 | 10/1985 | Japan. |
| 62/129853 | 11/1985 | Japan. |
| 62/201441 | 2/1986 | Japan. |
| 62/166331 | 7/1986 | Japan. |
| 62/75448 | 4/1987 | Japan. |
| 62/131259 | 6/1987 | Japan. |
| 63/250652 | 10/1988 | Japan. |
| 94/11784 | 5/1994 | WIPO. |

Primary Examiner—Lee C. Wright
Attorney, Agent, or Firm—Andrew J. Anderson

[57] ABSTRACT

Thermal and photochemical yellowing of a color photographic element, such as a color print, is inhibited by incorporating into the photographic element an ionizable epoxy compound having the formula:

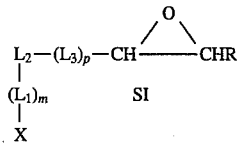

wherein:

R is H, alkyl, substituted alkyl, aryl, or substituted aryl;

$L_1$ is alkyl, substituted alkyl, aryl, or substituted aryl;

$L_2$ is O, CO, S, $SO_2$, $PO_2$, C(O)O, NHCO or $NHSO_2$;

$L_3$ is alkyl or substituted alkyl;

m is 0 or 1;

p is 0 or 1;

X is selected from the group consisting of

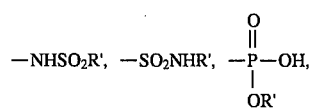

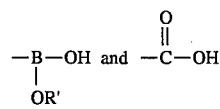

wherein:

R' is H, alkyl, substituted alkyl, aryl or substituted aryl, or, if $L_2$ comprises an ionizable group, X is alkyl, substituted alkyl, aryl or substituted aryl.

5 Claims, No Drawings

COLOR PHOTOGRAPHIC ELEMENT CONTAINING NEW EPOXY SCAVENGERS FOR RESIDUAL MAGENTA COUPLER

FIELD OF THE INVENTION

This invention relates to novel epoxy compounds useful in multilayer silver halide color photographic element, to a color photographic element having improved resistance to thermal and photochemical yellowing, and to a method of preparing said photographic element.

BACKGROUND OF THE INVENTION

It is well known that thermal and photochemical yellowing are major concerns in magenta image stability of color prints. Over the years improvement in magenta image stability has been achieved by introducing more efficient image stabilizers. However, there still exists a need to further improve the resistance to yellowing in color paper.

It has been known for some time that compounds having the generic structure S are able to undergo reaction with residual magenta coupler and thereby effectively prevent both thermal and photochemical yellowing since the products of the reaction are not yellow and are not prone to yellowing. However, a major problem in the utilization of these compounds is the loss of coupler during storage of the photographic element prior to exposure and processing resulting in a reduction in color density in the print. See for example, U.S. Pat. No. 4,540,657 to Krishnamurthy and Japanese Patent Publication No. 62- 131259 to Fuji Photo Film Co., Ltd.

Generic structure of Compound S is represented below:

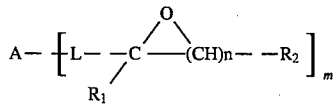

wherein:

A is a polyvalent atom, an acidic oxide group, a carboxylic group, a heterocyclic moiety, a carbocyclic group, or an alkane or substituted alkane group.

each L is at least one divalent linking group;

$R_1$ and $R_2$ are H, alkyl, cycloalkyl, aryl, heterocyclic, ester, n is a positive integer with a range of 1–6, m is a positive integer of at least one, with the proviso that at least one of A, L, $R_1$ or $R_2$ contains at least one ester or amide group derived from an acidic oxide of carbon, phosphorous, sulfur, boron or silicon.

In copending application Ser. No. 08/000,431, filed Jan. 4, 1993, we showed that the compound S-1 (having the structural formula set forth below) could be incorporated in a silver halide color photographic element containing a ballasted magenta coupler such that there is negligible loss of coupler prior to processing. This was achieved by coating the epoxy compound in a separate layers that were adjacent to the imaging layer containing the magenta coupler and the green sensitized emulsion. Furthermore, it has also been demonstrated that mixing of S-1 with residual magenta coupler after processing may be achieved by using a pH dependent solubilizing agent, e.g., a fatty acid, such as myrisitic acid, in the coating and processing the coating using developer which preferably contains benzyl alcohol. However, the use of benzyl alcohol in the developer raises serious environmental concerns. There is therefore a need to achieve post process mixing of the epoxy scavenger with the residual magenta coupler without using benzyl alcohol in the color developer.

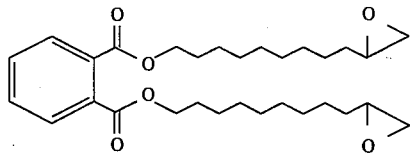

PROBLEM TO BE SOLVED BY THE INVENTION

It is desirable to improve the resistance to thermal and photochemical yellowing of color photographic elements, such as color paper, without the use of an external solubilizing agent such as benzyl alcohol.

SUMMARY OF THE INVENTION

An object of this invention is a silver halide based color photographic element having excellent image stability; particularly with respect to thermal and photochemical yellowing.

A further object of this invention is a silver halide based color photographic element containing a scavenger for residual magenta coupler.

A still further object of this invention is a method of incorporating a scavenger for residual magenta coupler in the above photographic element such that loss of coupler prior to processing is minimal.

A still further object of this invention is the use of novel epoxy scavenger compounds having the generic structure SI and a method of incorporating the compounds such that there is elimination of residual magenta after processing the photographic element in a color developer that contains no benzyl alcohol.

This realized by using novel epoxy scavenger compounds that contain a pH dependent ionizable group to facilitate migration of the scavenger from the adjacent scavenger layer (that does not contain any coupler) to the imaging layer (containing coupler and emulsion) at the pH of development.

One aspect of this invention comprises an epoxy compound having the following generic structure:

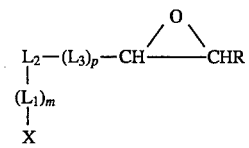

wherein:
R is H, alkyl, substituted alkyl, aryl, or substituted aryl;
$L_1$ is alkyl, substituted alkyl, aryl, or substituted aryl;
$L_2$ is O, CO, S, $SO_2$, $PO_2$, C(O)O, NHCO or $NHSO_2$;
$L_3$ is alkyl or substituted alkyl;
m is 0 or 1;
p is 0 or 1;
X is selected from the group consisting of

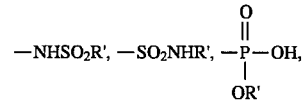

-continued $$-B-OH \text{ and } -\overset{O}{\underset{\|}{C}}-OH$$
$$\phantom{-B}|\phantom{OH}$$
$$\phantom{-B}OR'$$

wherein:

R' is H, alkyl, substituted alkyl, aryl or substituted aryl, or, if $L_2$ comprises an ionizable group, X is alkyl, substituted alkyl, aryl or substituted aryl.

A further aspect of this invention comprises a color photographic element comprising a support having coated thereon:

(a) a photosensitive first layer comprising
 (i) a silver halide emulsion and
 (ii) a magenta coupler dispersed therein; and
(b) a second layer comprising an epoxy compound of the above formula.

Yet another aspect of this invention comprises a method of preparing a color photographic element comprising coating on a support (a) a photosensitive first layer comprising
 (i) a silver halide emulsion and
 (ii) a magenta coupler dispersed therein; and
(b) a second layer comprising an epoxy compound of the above formula.

ADVANTAGEOUS EFFECT OF THE INVENTION

The novel ionizable epoxy compounds can be added to a photographic element to inhibit the thermal and photochemical yellowing of color photographic elements.

DETAILED DESCRIPTION OF THE INVENTION

As noted above, the novel epoxy compounds of this invention have the following general structural formula:

$$\underset{\underset{\underset{X}{|}}{\underset{(L_1)_m}{|}}}{L_2-(L_3)_p-CH}\overset{O}{\overset{/\diagdown}{\text{———}}}CHR \qquad \text{SI}$$

wherein:
R is H, alkyl, substituted alkyl, aryl, or substituted aryl;
$L_1$ is alkyl, substituted alkyl, aryl, or substituted aryl;
$L_2$ is O, CO, S, $SO_2$, $PO_2$, C(O)O, NHCO or $NHSO_2$;
$L_3$ is alkyl or substituted alkyl;
m is 0 or 1;
p is 0 or 1;
X is selected from the group consisting of $$-NHSO_2R', \; -SO_2NHR', \; -\overset{O}{\underset{\underset{OR'}{|}}{\overset{\|}{P}}}-OH,$$

$$-B-OH \text{ and } -\overset{O}{\underset{\underset{}{|}}{\overset{\|}{C}}}-OH$$
$$\phantom{-B}|$$
$$\phantom{-B}OR'$$

wherein:
R' is H, alkyl, substituted alkyl, aryl or substituted aryl, or, if $L_2$ comprises an ionizable group, X is alkyl, substituted alkyl, aryl or substituted aryl.

Substituents on the alkyl and/or aryl groups can be hydrocarbyl groups, one or more hetero atoms, such as chlorine and the like or one or more hetero groups containing for example, N, P, S, etc.

Preferred compounds have the generic structural formula:

[Structure: 4-(NHSO$_2$R')-phenyl ester of an ω-epoxy fatty acid, with $-(CH_2)_n-$ chain and terminal epoxide with R substituent]

wherein:
R is H, alkyl, substituted alkyl, aryl, or substituted aryl, and
R' is H, alkyl, substituted alkyl, aryl or substituted aryl; and n is 2 to 20.

R is preferably H or alkyl, such as methyl, etc. R' is preferably substituted phenyl, such as p-chlorophenyl.

A general scheme for the synthesis of these preferred compounds is given below:

[Scheme: p-aminophenol + RSO$_2$Cl → (MeCN/Py) → p-(NHSO$_2$R)-phenol (A)]

A + ClCO(CH$_2$)$_8$CH=CH$_2$ $\xrightarrow{\text{THF/Et}_3\text{N}}$

[Structure B: 4-(NHSO$_2$R)-phenyl ester of 10-undecenoic acid, $-(CH_2)_8$CH=CH$_2$]

B + [m-chloroperoxybenzoic acid, CO$_3$H on chlorobenzene] $\xrightarrow[\text{0–25° C.}]{\text{CH}_2\text{Cl}_2}$

[Structure: 4-(NHSO$_2$R)-phenyl ester of 10,11-epoxyundecanoic acid]

R = substituted alkyl or aryl

Illustrative epoxy compounds of this invention are:

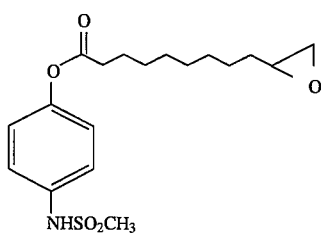 SI-1
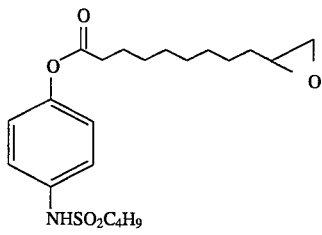 SI-2
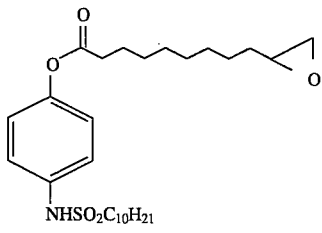 SI-3
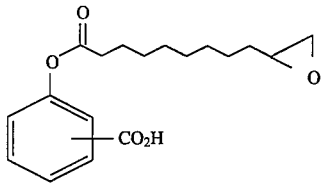 SI-4
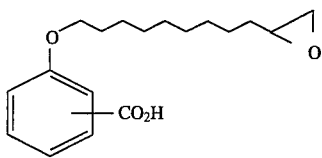 SI-5
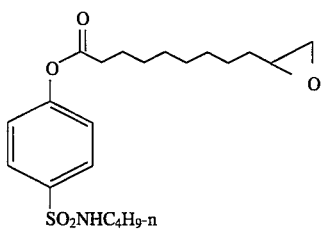 SI-6
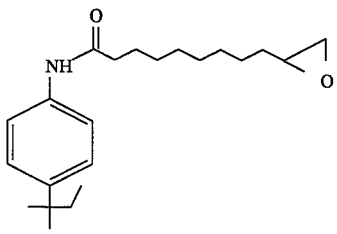 SI-7

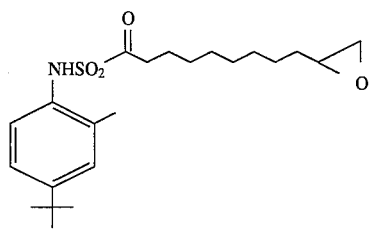
SI-8
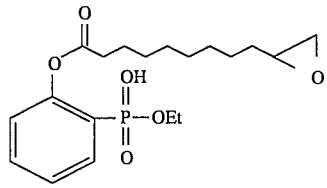
SI-9
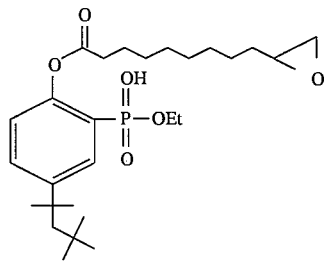
SI-10
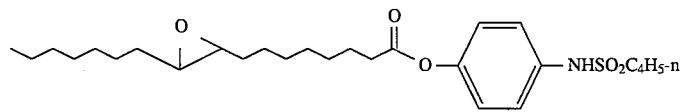
SI-11
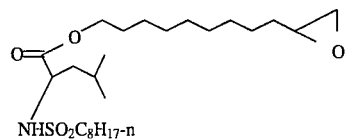
SI-12
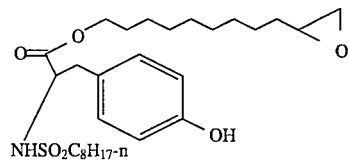
SI-13
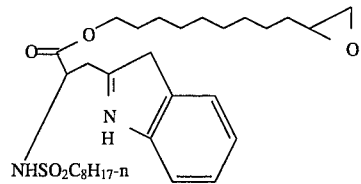
SI-14
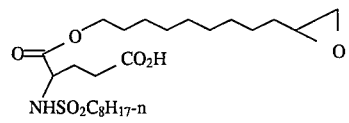
SI-15
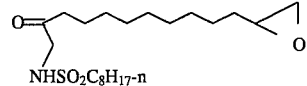
SI-16

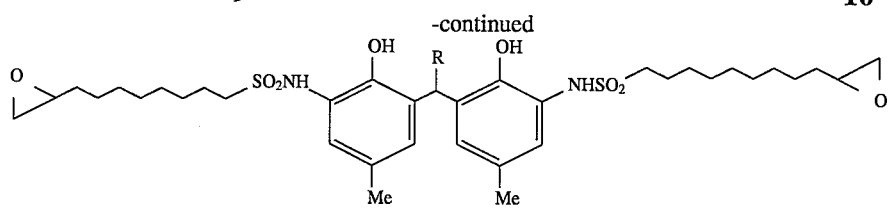
SI-17
[R=H, Me]
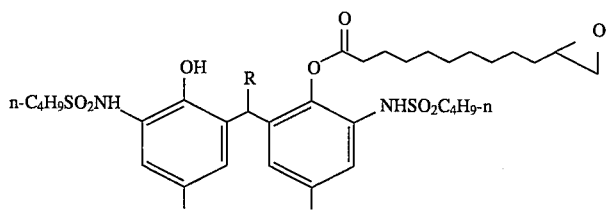
SI-18
[R=H, Me]
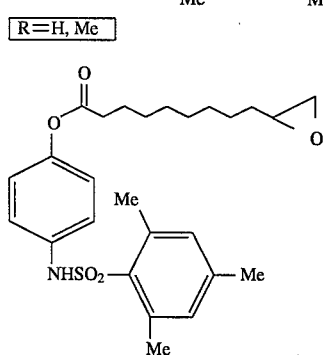
SI-19
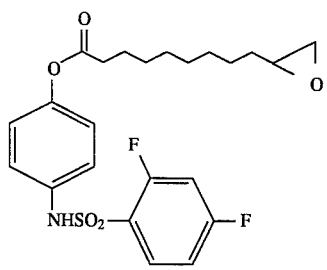
SI-20
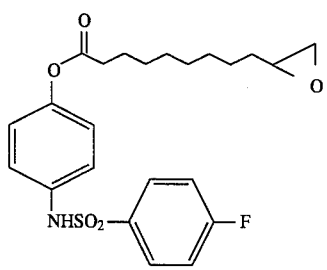
SI-21
Specific compounds of the most preferred structure of SI are:
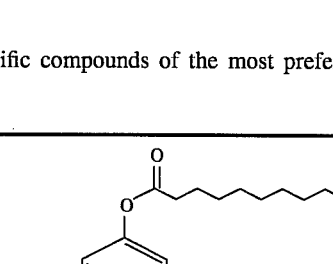
wherein:
| R | Compound Number |
|---|---|
| n-C₄H₉ | SI-2 |
| Me-⌬(Me)(Me) (mesityl) | SI-19 |

Physical properties of selected SI compounds having the formula set forth below with R as defined in the following table are:

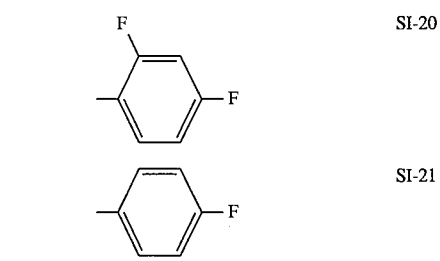

Melting Points and Log P values for Selected Examples

| SI-n | R | mp (°C.) | Log P* |
|---|---|---|---|
| (SI-1) | —CH₃ | 100–101 | 2.7 |
| (SI-2) | n-C₄H₉ | 69–70 | 4.3 |
| (SI-3) | n-C₁₀H₂₁ | 88–89 | 7.5 |
| (SI-19) | 2,4,6-trimethylphenyl (Me, Me, Me) | 77–78 | 5.9 |
| (SI-20) | 2,4-difluorophenyl | 77(s) | 4.5 |
| (SI-21) | 4-fluorophenyl | 56–69 | 4.6 |
| (S-1) (Comparative) | bis-CO₂(CH₂)₉CH—O on phenyl | oil | 7.0 |

*Log P values are calculated values of the octanol/water partition coefficient of the compound and were calculated using Med Chem v. 3.54, a software package available from the Medicinal Chemistry Project, Pomona College, Claremont, California.

The magenta dye forming coupler is preferably a pyrazolone, pyrazolotriazole, pyrazolobenzimidazole with or without a suitable leaving group. The magenta coupler can be monomeric, dimeric, trimeric, oligomeric or polymeric coupler wherein the coupler moiety can be attached to the polymeric backbone via a substituent on the coupler moiety or a substituent on a coupling off group. Illustrative magenta couplers are disclosed in, for example, U.S. Pat. Nos. 1,969,479; 2,311,082; 2,343,703; 2,369,489; 2,575,182; 2,600,788; 2,706,685; 2,908,573; 3,061,432; 3,062,653; 3,152,896; 3,153,816; 3,214,437; 3,253,924; 3,311,476; 3,419,391; 3,519,429; 3,725,067; 3,770,447; 3,907,571; 3,928,044; 3,935,015; 4,120,723; 4,123,281; 4,199,361; 4,336,325; 4,351,897; 4,385,111; 4,401,752; 4,407,936; 4,413,054; 4,283,472; 4,338,393; 4,420,556; 4,443,536; 4,500,630; 4,522,915; 4,540,654; 4,576,912; 4,581,326; 4,621,046; 4,728,598; 4,774,172; and 4,853,319 European Patent Applications Nos. 284,239; 284,240; 240,852; 170, 164; and 177,765; Japanese Patent Publication Nos. 60/170854, 60/194451 and 60/194452 and Great Britain Patents Nos. 1,047,612, 1,357,372 and 1,530,272, and "Farbkuppler-eine Literaturübersicht", published in Agfa Mitteilungen, Band III, pp 126–156 (1961); the disclosures of which are incorporated herein by reference.

Magenta dye-forming couplers comprise pyrazolone compounds of the general formulae:

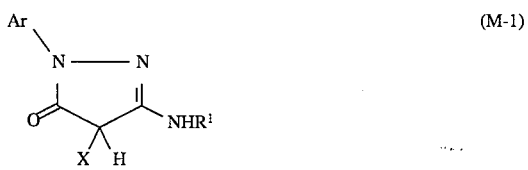

(M-1)

and

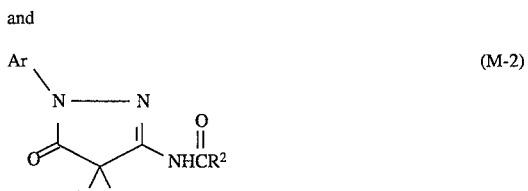

(M-2)

pyrazolotriazole compounds of the general formulae:

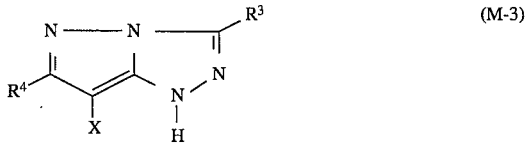

(M-3)

and

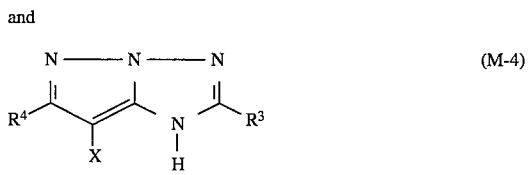

(M-4)

and pyrazolobenzimidazoles of the formula:

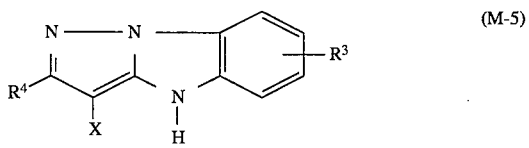

(M-5)

wherein

Ar is an unsubstituted aryl group or an aryl group (including pyridyl) substituted with one or more substituents selected from halogen atoms and cyano, alkylsulfonyl, arylsulfonyl, sulfamoyl, sulfonamido, carbamoyl, carbonamido, alkoxy, acyloxy, aryloxy, alkoxycarbonyl, aryloxycarbonyl, ureido, nitro, alkyl, and trifluoromethyl, or Ar is an aryl group substituted with a group which forms a link to a polymeric chain;

$R^1$ is a substituted or unsubstituted phenyl group and $R^2$ is a substituted or unsubstituted alkyl or phenyl group, the $R^1$ and $R^2$ substituents being individually selected from halogen atoms, and alkyl, aryl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyl, acyloxy, ureido, imido, carbamate, heterocyclic, cyano, trifluoromethyl, alkylthio, nitro, carboxyl and hydroxyl groups, provided that $R^1$ and $R^2$ each contain at least 6 carbon atoms or the $R^1$ and $R^2$ substituents may individually comprise a group which forms a link to a polymeric chain;

$R^3$ and $R^4$ are individually selected from the group consisting of hydrogen, substituted and unsubstituted alkyl, substituted and unsubstituted phenyl, substituted and unsubstituted alkoxy, substituted and unsubstituted amino, substituted and unsubstituted anilino, substituted and unsubstituted acylamino, halogens and a group which links to a polymer, provided that the total number of carbon atoms contained in $R^3$ and $R^4$ is at least 6 if neither $R^3$ nor $R^4$ is a group which links to a polymer; and X is hydrogen or a coupling-off group selected from the group consisting of halogens, alkoxy, aryloxy, alkylthio, arylthio, acyloxy, sulfonamido, carbonamido, arylazo, nitrogen-containing heterocyclic and imido groups. Coupling-off groups are well known to those skilled in the photographic art. Generally, such groups determine the equivalency of the coupler and modify the reactivity of the coupler. Coupling-off groups can also advantageously effect the layer in which the coupler is coated or other layers in the photographic material by performing, after release from the coupler, such functions as development inhibition, bleach acceleration, color correction, development acceleration and the like. Representative coupling-off groups include, as noted above, halogens (for example, chloro), alkoxy, aryloxy, alkyl thio, aryl thio, acyloxy, sulfonamido, carbonamido, arylazo, nitrogen-containing heterocyclic groups such as pyrazolyl and imidazolyl, and imido groups such as succinimido and hydantoinyl groups. Except for the halogens, these groups may be substituted if desired. Coupling-off groups are described in further detail in: U.S. Pat. Nos. 2,355,169; 3,227,551; 3,432,521; 3,476,563; 3,617,291; 3,880,661; 4,052,212 and 4,134,766, and in British Patent References Nos. 1,466,728; 1,531,927; 1,533,039; 2,006,755A and 2,017,704A, the disclosures of which are incorporated herein by reference.

Preferred structures of magenta couplers are 4- or 2-equivalent pyrazolone couplers, particularly couplers of the structure:

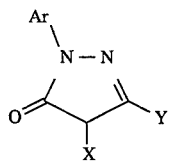
(M-6)

wherein:

Ar is selected from the group consisting of unsubstituted aryl groups, substituted aryl groups and substituted pyridyl groups, the substituents being selected from the group consisting of halogen atoms and cyano, alkylsulfonyl, arylsulfonyl, sulfamoyl, sulfamido, carbamoyl, carbonamido, alkoxy, acyloxy, aryloxy, alkoxycarbonyl, aryloxycarbonyl, ureido, nitro, alkyl and trifluoromethyl groups;

Y is an anilino group substituted with one or more substituents selected from the group consisting of halogen atoms, and alkyl, aryl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyl, acyloxy, ureido, imido, carbamate, heterocyclic, cyano, hydroxyl groups, and groups which form a link to a polymeric chain, and wherein Y contains at least 6 carbon atoms; and X is a coupling-off group selected from the group consisting of halogen, alkoxy, aryloxy, alkylthio, arylthio, acyloxy, sulfonamido, sulfonyloxy, carbonamido, arylazo, nitrogen-containing heterocyclic and imido groups.

Coupling-off groups are well known to those skilled in the photographic art. Generally, such groups determine the equivalency of the coupler and modify the reactivity of the coupler. Coupling-off groups can also advantageously effect the layer in which the coupler is coated or other layers in the photographic material by performing, after release from the coupler, such functions as development inhibition, bleach acceleration, color correction, development acceleration and the like. Representative coupling-off groups include, as noted above, halogens (for example, chloro), alkoxy, aryloxy, alkylthio, arylthio, acyloxy, sulfonamido, carbonamido, arylazo, nitrogen-containing heterocyclic groups such as pyrazolyl and imidazolyl, and imido groups such as succinimido and hydantoinyl groups. Coupling-off groups are described in further detail in: U.S. Pat. Nos. 2,355,169; 3,227,551; 3,432,521; 3,476,563; 3,67,291; 3,880,661; 4,052,212 and 4,134,766, and in British Patent Reference Nos. 1,466,788; 1,531,927; 1,533,039; 2,006,755A and 2,017,704A, the disclosures of which are incorporated herein by reference.

Particularly preferred are compounds in which Ar is of the structure:

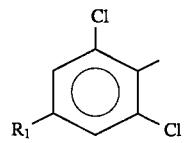

wherein $R_1$ is selected from the group consisting of halogen, cyano, alkylsulfonyl, arylsulfonyl, sulfamoyl, sulfonamido, carbamoyl, carbonamido, ureido, alkoxycarbonyl, aryloxycarbonyl, acyloxy, alkoxy, aryloxy, nitro and trifluoromethyl groups;

Y is of the structure:

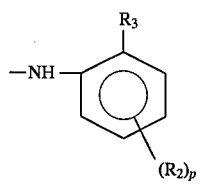

wherein p is from zero to 2 and each $R_2$ is in a meta or para position with respect to $R_3$;

each $R_2$ is individually selected from the group consisting of halogen, alkyl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyloxy, ureido, imido, carbamate, heterocyclic, cyano, nitro, acyl, trifluoromethyl, alkylthio and carboxyl groups; and $R_3$ is selected from the group consisting of hydrogen, halogen, alkyl, alkoxy, aryloxy, alkylthio, carbonamido, carbamoyl, sulfonamido, sulfamoyl, alkylsulfonyl, arylsulfonyl, alkoxycarbonyl, acyloxy, acyl, cyano, nitro and trifluoromethyl groups; and X is of the structure:

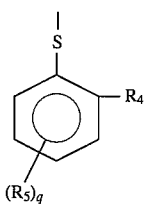

wherein $R_4$ and $R_5$ are individually selected from the group consisting of hydrogen, halogen, alkyl, alkoxy, aryloxy, carbonamido, ureido, carbamate, sulfonamido, carbamoyl, sulfamoyl, acyloxy, alkoxycarbonyl, aryloxycarbonyl, amino and carboxyl groups, and wherein q is 0, 1 or 2 and $R_5$ may be in the meta or para position with respect to the sulfur atom.

Suitable magenta dye-forming couplers for use in the compositions and methods of the present invention include, but are not limited to, the following compounds:

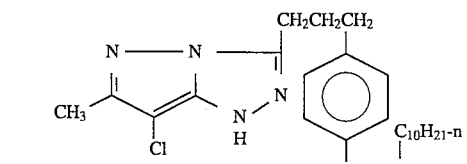
(M-7)

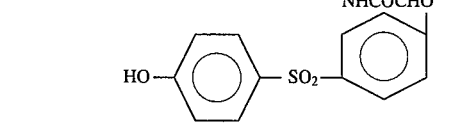
(M-8)

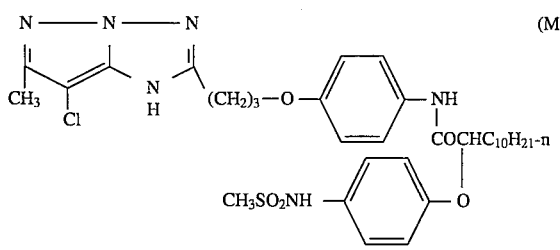
(M-9)

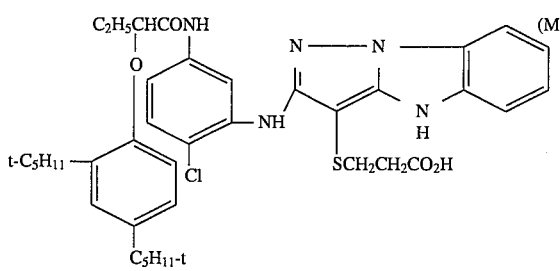
(M-10)

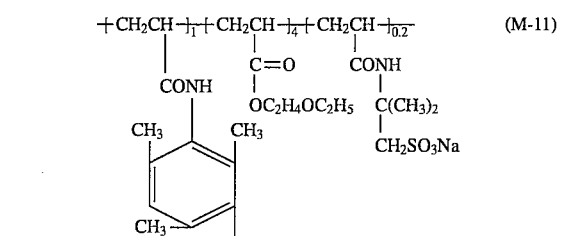
(M-11)

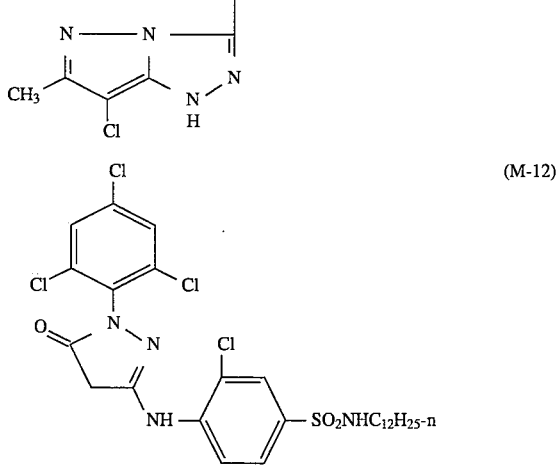
(M-12)

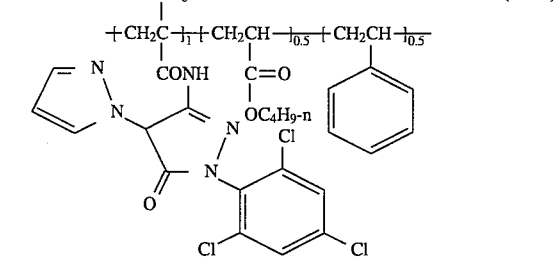
(M-13)

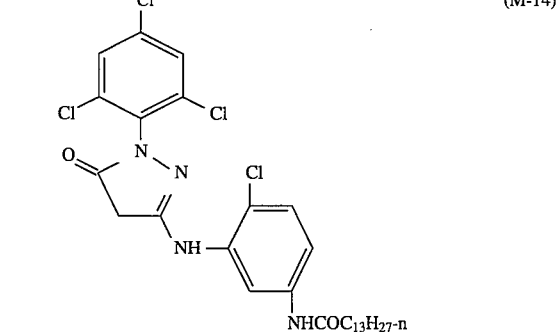
(M-14)

(M-15)
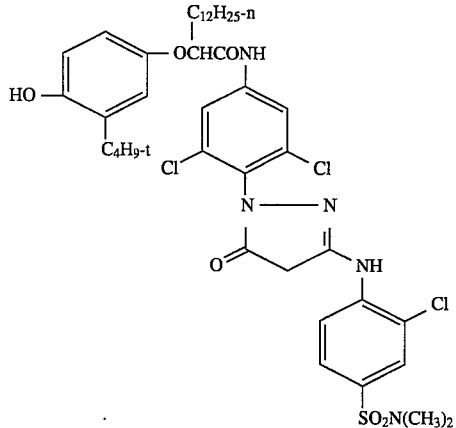
(M-16)
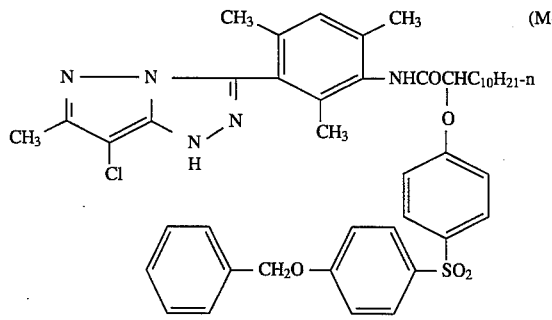
(M-17)
(M-18)
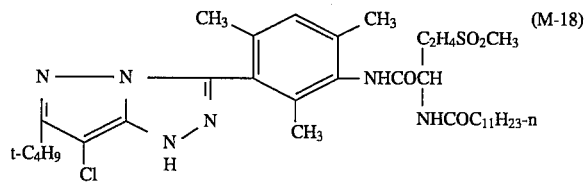
Examples of two-equivalent 3-anilino pyrazolone dye-forming magenta couplers suitable for use in the coupler compositions of the present invention include, but are not limited to the following:
(M-19)
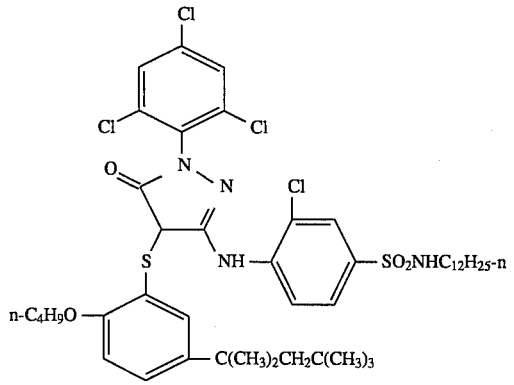

(M-20)
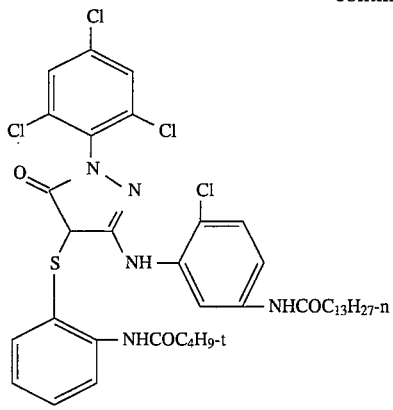
(M-21)
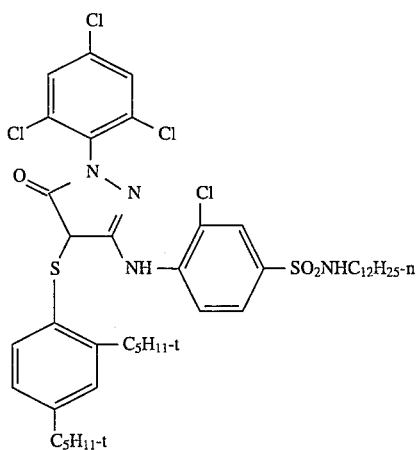
(M-22)
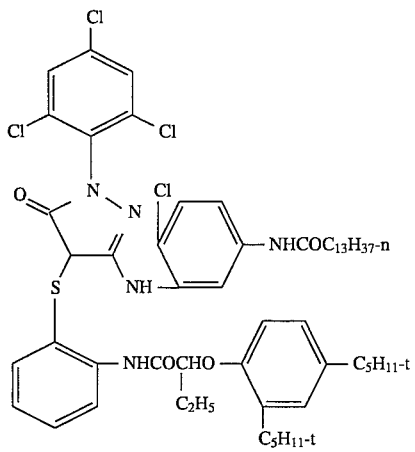

-continued
(M-23)
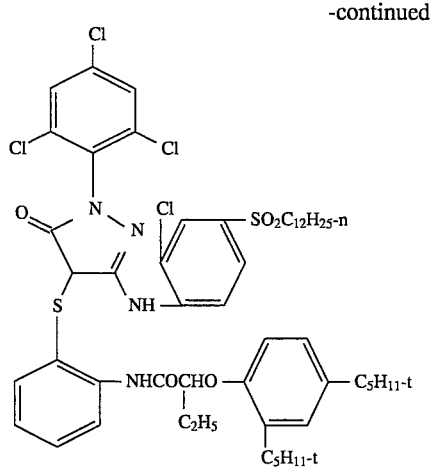
(M-24)
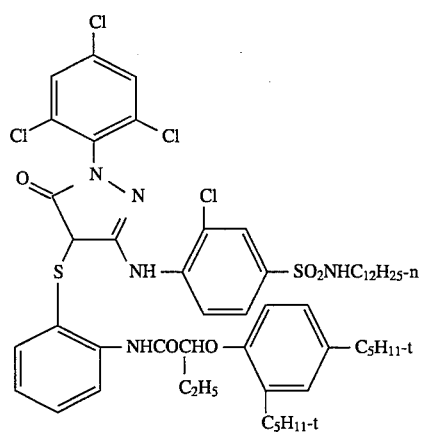
(M-25)
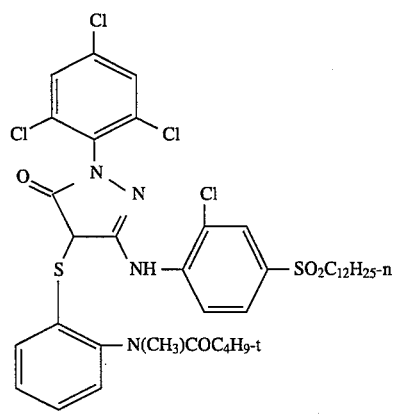
(M-26)
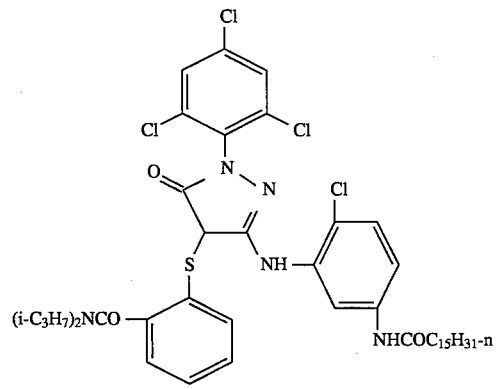

(M-27)
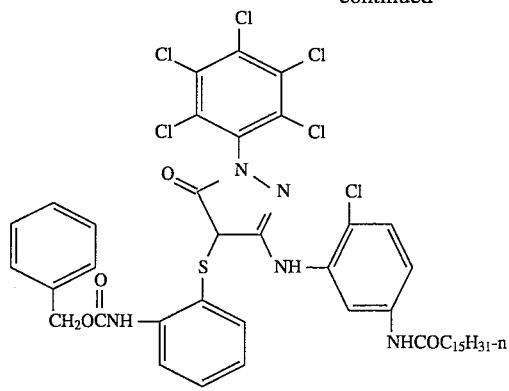
(M-28)
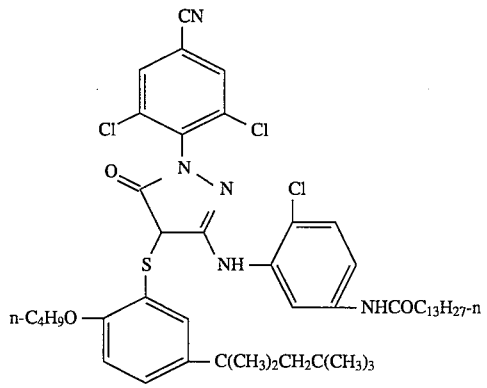
(M-29)
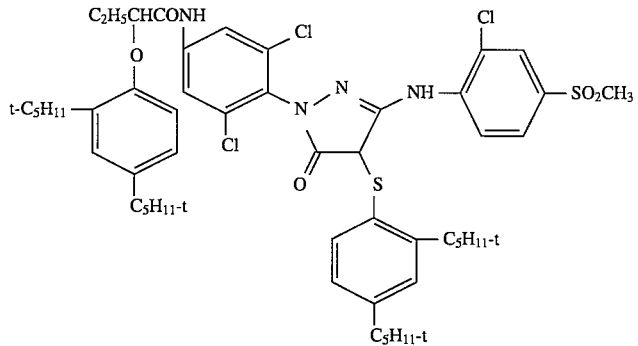
(M-30)

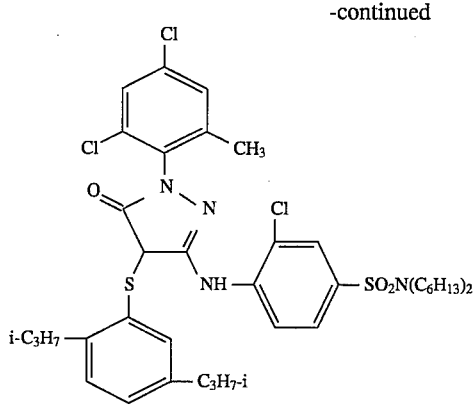
(M-31)
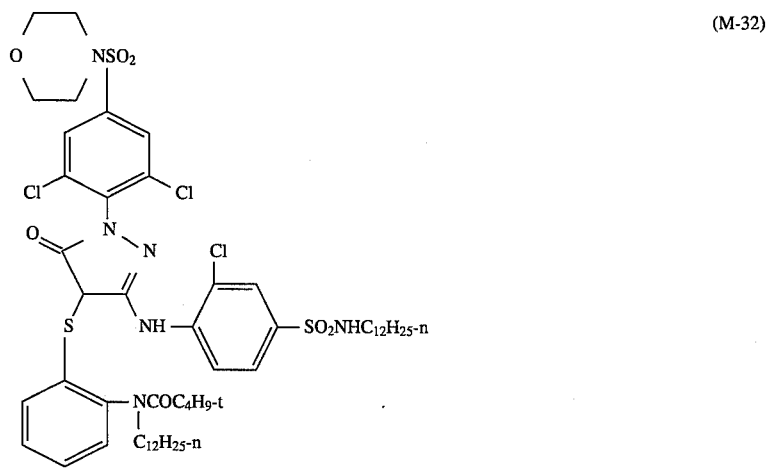
(M-32)
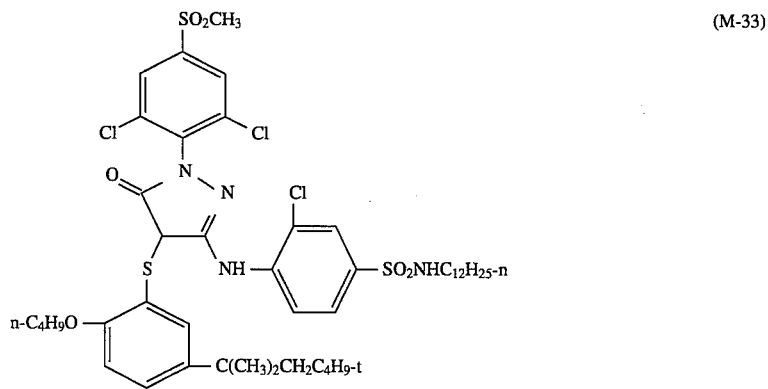
(M-33)
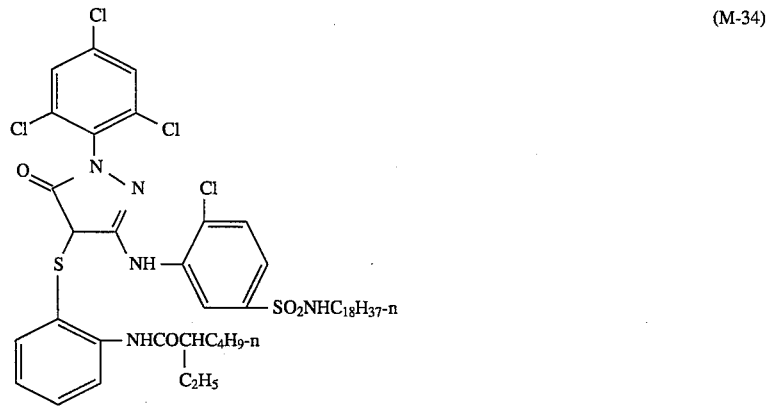
(M-34)

-continued
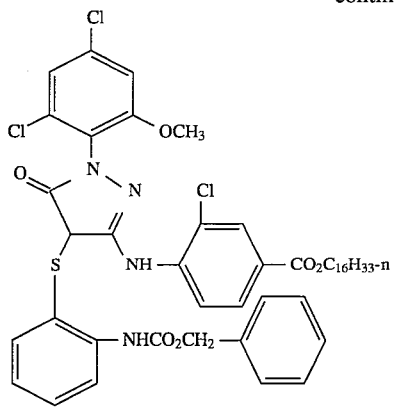
(M-35)
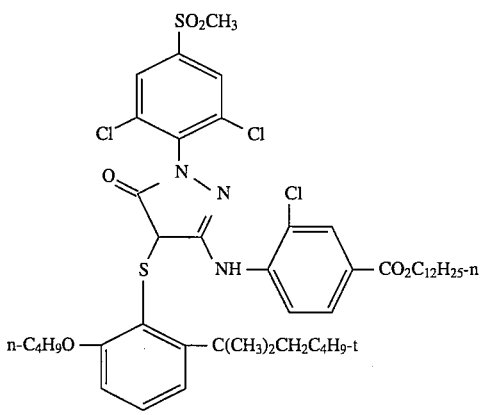
(M-36)
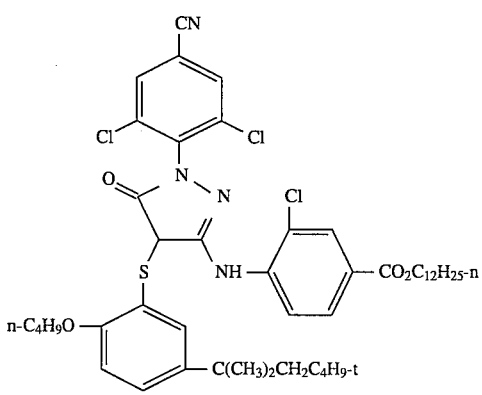
(M-37)
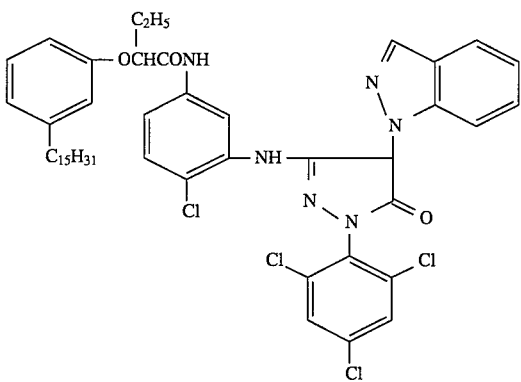
(M-38)

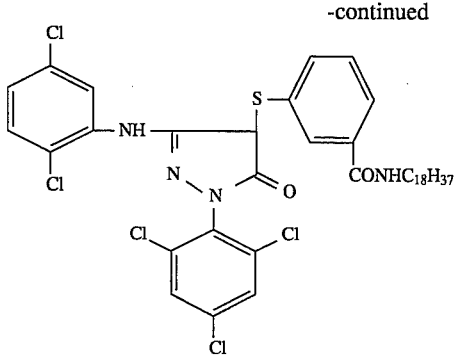

(M-39)

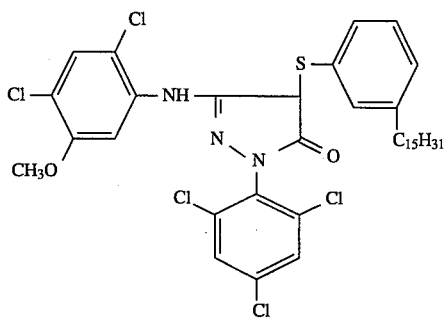

(M-40)

Particularly preferred couplers are the compounds of the formulae:

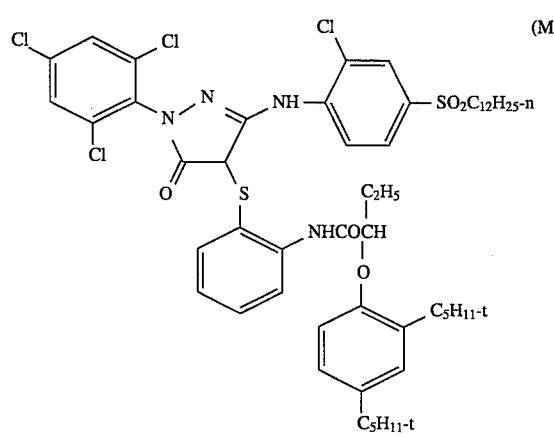

(M-23)

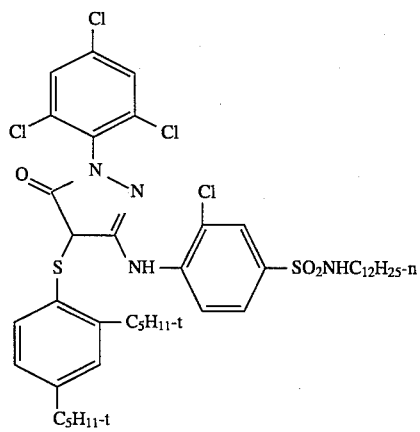

(M-21)

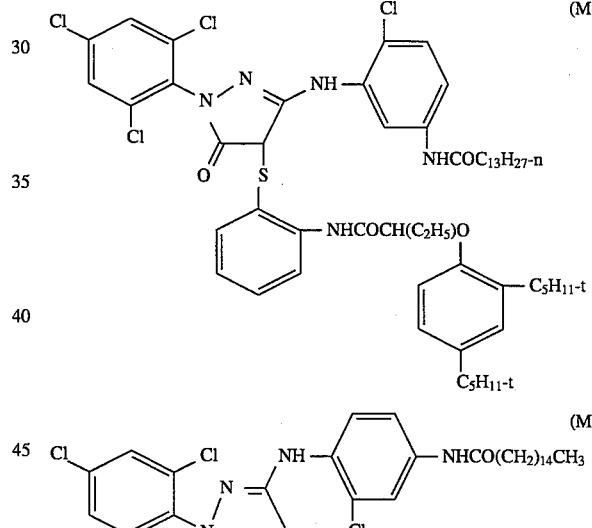

(M-22)

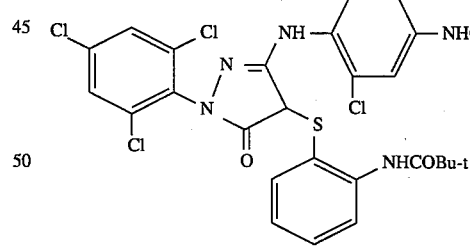

(M-20)

The color photographic element of this invention comprises, in addition to the magenta coupler-containing layer and the layer comprising the epoxy compound, various other layers typically included in color photographic elements.

Multicolor color photographic elements typically contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND.

In the following discussion of suitable materials for use in the photographic element of this invention, reference will be made to *Research Disclosure*, December 1989, Item 308119, available as described above, which will be identified hereafter by the term "Research Disclosure." The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections V and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

The photographic element of this invention generally contains image dye-forming couplers that form cyan dyes upon reaction with oxidized color developing agents which are described in such representative patents and publications as: U.S. Pat. Nos. 2,772,162, 2,895,826, 3,002,836, 3,034,892, 2,474,293, 2,423,730, 2,367,531, 3,041,236, 4,883,746 and "Farbkuppler-eine Literature Ubersicht," published in Agfa Mitteilungen, Band III, pp. 156–175 (1961). Preferably such couplers are phenols and naphthols that form cyan dyes on reaction with oxidized color developing agent.

As discussed above, the photographic element of this invention contains an image dye-forming coupler that forms a magenta dye. Illustrative magenta couplers are set forth above.

The photographic element can also contain couplers that form yellow dyes upon reaction with oxidized and color developing agent are described in such representative patents and publications as: U.S. Pat. Nos. 2,875,057, 2,407,210, 3,265,506, 2,298,443, 3,048,194, 3,447,928 and "Farbkuppler-eine LiteraturUbersicht," published in Agfa Mitteilungen, Band III, pp. 112–126 (1961). Such couplers are typically open chain ketomethylene compounds.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may also be used in association with "wrong" colored couplers (e.g. to adjust levels of interlayer correction) and, in color negative applications, with masking couplers such as those described in EP 213.490; Japanese Published Application 58–172,647; U.S. Pat. No. 2,983,608; German Application DE 2,706,117C; U.K. Patent 1,530,272; Japanese Application A-113935; U.S. Pat. Nos. 4,070,191 and 4,273,861; and German Application DE 2,643,965. The masking couplers may be shifted or blocked.

The photographic element can also contain materials that accelerate or otherwise modify the processing steps e.g. of bleaching or fixing to improve the quality of the image. Bleach accelerator releasing couplers such as those described in EP 193,389; EP 301,477; U.S. Pat. No. 4,163,669; U.S. Pat. No. 4,865,956; and U.S. Pat. No. 4,923,784, may be useful. Also contemplated is use of nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

For example, in a color paper format, the photographic element of the invention may comprise a support bearing the following layers from top to bottom:

(1) one or more overcoats;

(2) a cyan layer containing "Coupler 1": Butanamide, 2-(2,4-bis(1,1-dimethylpropyl)phenoxy)-N-( 3,5-dichloro-2-hydroxy-4-methylphenyl)-, "Coupler 2": Acetamide, 2-(2, 4-bis(1,1-dimethylpropyl)phenoxy)-N-( 3,5-dichloro-2-hydroxy-4-, and UV Stabilizers: Phenol, 2-(5-chloro-2H-benzotriazol-2-yl)-4,6-bis(1,1 -dimethylethyl)-; Phenol, 2-(2H-benzotriazol-2-yl)-4-( 1,1-dimethylethyl)-; Phenol, 2-(2H-benzotriazol-2-yl)- 4-(1,1-dimethylethyl)-6-(1-methylpropyl)-; and Phenol, 2-(2H-benzotriazol-2-yl)-4,6-bis(1, 1-dimethylpropyl)- and a poly(t-butylacrylamide) dye stabilizer;

(3) an interlayer;

(4) a magenta layer containing "Coupler 3": Octanamide, 2-[2,4-bis(1,1-dimethylpropyl)phenoxy]-N-[2-(7-chloro-6-methyl-1H-pyrazolo[1,5-b][1,2,4]triazol- 2-yl)propyl]- together with 1,1'-Spirobi(1H-indene), 2,2',3,3'-tetrahydro-3,3,3',3'-tetramethyl-5,5',6,6'-tetrapropoxy-;

(5) an interlayer; and (6) a yellow layer containing "Coupler 4": 1-Imidazolidineacetamide, N-(5-((2-(2,4-bis(1,1 -dimethylpropyl)phenoxy)-1-oxobutyl)amino)-2 -chlorophenyl)-.alpha.-(2,2-dimethyl-1-oxopropyl)-4 -ethoxy-2,5-dioxo-3-(phenylmethyl)-.

The photographic element of the invention can also contain filter dye layers comprising colloidal silver sol or yellow, cyan, and/or magenta filter dyes, either as oil-in-water dispersions, latex dispersions or as solid particle dispersions. Additionally, the photographic element can contain "smearing" couplers (e.g. as described in U.S. Pat. No. 4,366,237; EP 96,570; U.S. Pat. No. 4,420,556; and U.S. Pat. No. 4,543,323.)

The photographic element can also contain image-modifying compounds such as "Developer Inhibitor-Releasing" compounds (DIR's). DIR's useful in conjunction with the compositions of the invention are known in the art and examples are described in U.S. Pat. Nos. 3,137,578; 3,148, 022; 3,148,062; 3,227,554; 3,384,657; 3,379,529; 3,615, 506; 3,617,291; 3,620,746; 3,701,783; 3,733,201; 4,049, 455; 4,095,984; 4,126,459; 4,149,886; 4,150,228; 4,211, 562; 4,248,962; 4,259,437; 4,362,878; 4,409,323; 4,477, 563; 4,782,012; 4,962,018; 4,500,634; 4,579,816; 4,607, 004; 4,618,571; 4,678,739; 4,746,600; 4,746,601; 4,791, 049; 4,857,447; 4,865,959; 4,880,342; 4,886,736; 4,937, 179; 4,946,767; 4,948,716; 4,952,485; 4,956,269; 4,959, 299; 4,966,835; 4,985,336 as well as in patent publications GB 1,560,240; GB 2,007,662; GB 2,032,914; GB 2,099, 167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering,* Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

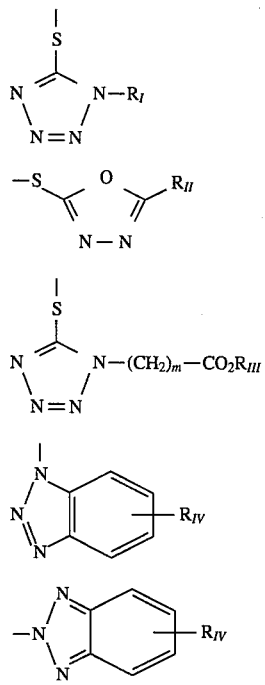

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group which produces the time-delayed release of the inhibitor group such as groups utilizing the cleavage reaction of a hemiacetal (U.S. Pat. No. 4,146,396, Japanese Applications 60- 249148; 60-249149); groups using an intramolecular nucleophilic substitution reaction (U.S. Pat. No. 4,248,962); groups utilizing an electron transfer reaction along a conjugated system (U.S. Pat. Nos. 4,409,323; 4,421,845; Japanese Applications 57-188035; 58-98728; 58-209736; 58-209738) groups utilizing ester hydrolysis (German Patent Application (OLS) No. 2,626,315); groups utilizing the cleavage of imino ketals (U.S. Pat. No. 4,546,073); groups that function as a coupler or reducing agent after the coupler reaction (U.S. Pat. No. 4,438,193; U.S. Pat. No. 4,618,571) and groups that combine the features describe above. It is typical that the timing group or moiety is of one of the formulas:

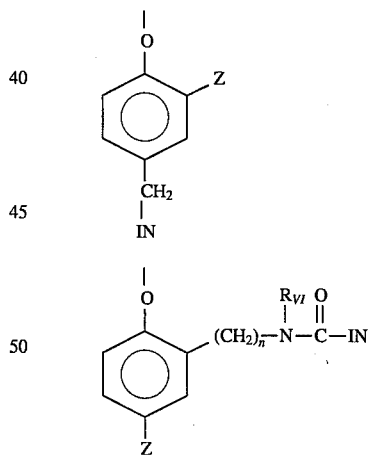

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

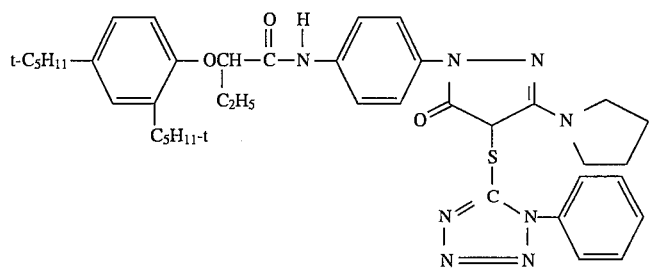
D1
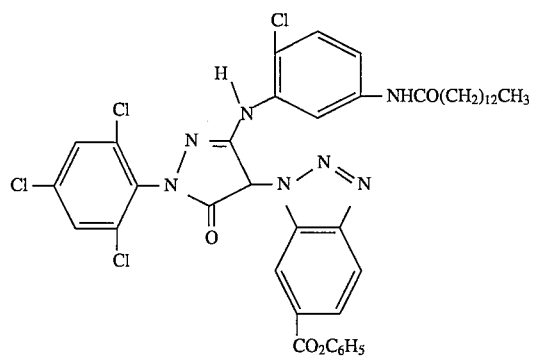
D2
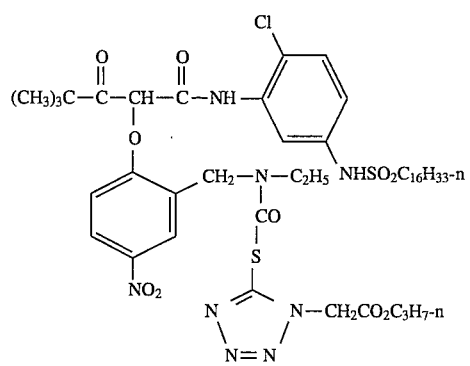
D3
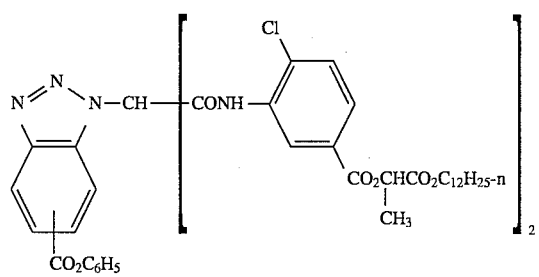
D4
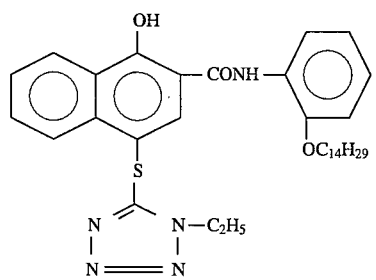
D5

D6
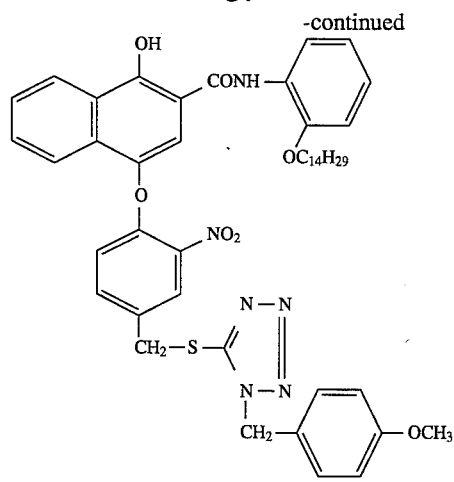
D7
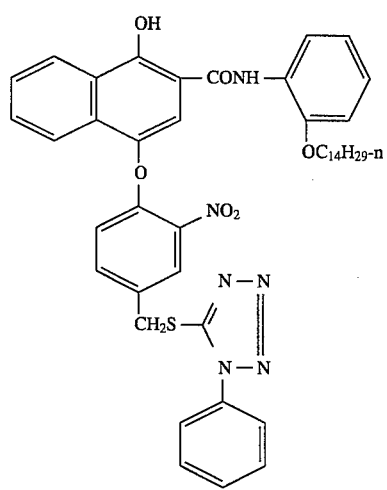
D8
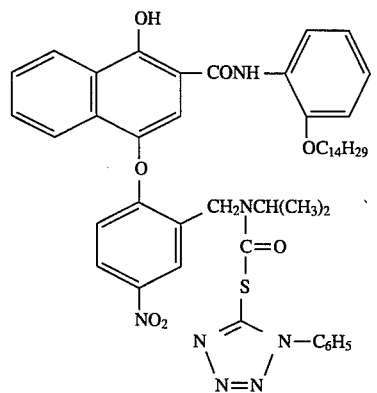

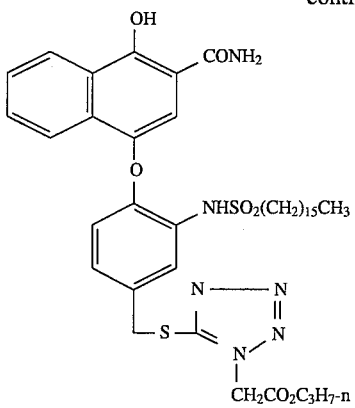

D9

-continued

It is also contemplated that the concepts of the present invention may be employed to obtain reflection color prints as described in Research Disclosure, November 1979, Item 18716, available from Kenneth Mason Publications, Ltd, Dudley Annex, 12a North Street, Emsworth, Hampshire P0101 7DQ, England, incorporated herein by reference. Other compounds that can be included in the photographic element of this invention are disclosed in Japanese Published Applications described in Derwent Abstracts having accession numbers as follows: 90-072,629, 90-072,630; 90-072,631; 90-072,632; 90-072,633; 90-072,634; 90- 077,822; 90-078,229; 90-078,230; 90-079,336; 90- 079,337; 90-079,338; 90-079,690; 90-079,691; 90- 080,487; 90-080,488; 90-080,489; 90-080,490; 90- 080,491; 90-080,492; 90-080,494; 90-085,928; 90- 086,669; 90-086,670; 90-087,360; 90-087,361; 90- 087,362; 90-087,363; 90-087,364; 90-088,097; 90- 093,662; 90-093,663; 90-093,664; 90-093,665; 90- 093,666; 90-093,668; 90-094,055; 90-094,056; 90- 103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where

ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616. In addition, use of [100] silver chloride emulsions as described in EP 534,395 are specifically contemplated.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

The photographic elements can be processed, for example, in accordance with color print processes such a the RA-4 process of Eastman Kodak Company as described in the British Journal of Photography Annual of 1988, Pp 198–199.

Preferred color developing agents are p-phenylenediamines such as:
4-amino-N,N-diethylaniline hydrochloride,
4-amino-3-methyl-N,N-diethylaniline hydrochloride,
4-amino-3-methyl-N-ethyl-N-(b-(methanesulfonamido) ethyl)aniline sesquisulfate hydrate,
4-amino-3-methyl-N-ethyl-N-(b-hydroxyethyl)aniline sulfate,
4-amino-3-b-(methanesulfonamido)ethyl-N,N-diethylaniline hydrochloride and
4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The following examples illustrate the invention:

EXAMPLE 1

Synthesis of SI-19

Reaction of p-Aminophenol with 2-Mesitylenesulfonyl Chloride. Synthesis of 4A

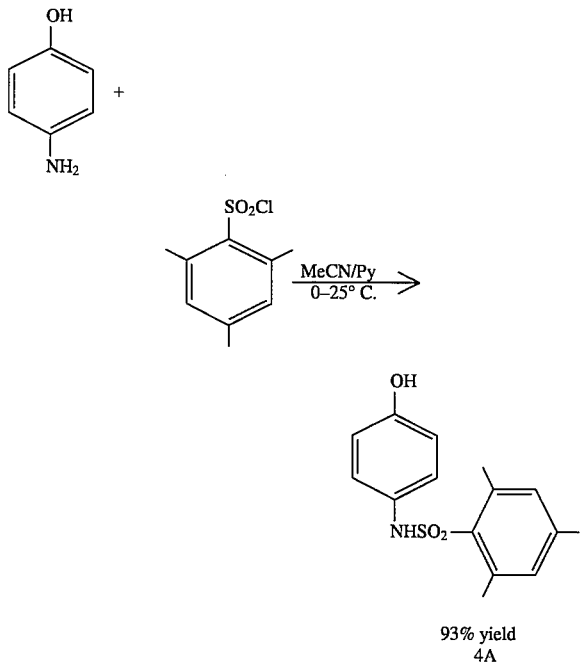

93% yield
4A

A 1 L flask equipped with a magnetic stirring bar and a pressure equalized addition funnel was charged with p-aminophenol (12.47 g, 114.31 mmol), and MeCN (200 mL). This solution was chilled in a ice/water bath for 10 minutes while stirring an Argon atmosphere. To this cold tan solution pyridine (9.22 g, 116.60 mmol) was added and the let stirred for 20 minutes. A pressure equalized addition funnel was charged with 2-mesitylenesulfonyl chloride (25.0 g, 114.31 mmol) with 90 mL of MeCN. The sulfonyl chloride solution was then added dropwise over 30 minutes. A color change from red to amber was observed during addition; the formation of a white precipitate was also noted. The reaction was stirred at room temperature until reaction was complete by tlc analysis (16 hours). Reaction mixture was poured into ice water (500 mL) and partitioned with EtOAc (200 mL), and transferred to separatory funnel. Layers were separated and aqueous layer was extracted with EtOAc (2×100 mL), organic layers were combined, washed with Sat. NH$_4$Cl (1×250 mL), brine (1×250 mL), dried over MgSO$_4$, filtered and stripped to give an off white solid (32.77 g). Crude product was recrystallized from EtOAc/hexanes to give two crops of 4A, as a white crystalline solid.mp 189°–190° C., (30.95 g, 93%) $^1$HNMR (300 MHz) DMSO; δ2.16 (s, 3H), 2.40 (s, 6H), (d, J=8.4 Hz, 2H), 6.72 (d, J=8.4 Hz, 2H), 6.90 (s, 2H), 9.28 (s, 1H), 9.47 (s, 1H). Anal. Calcd for C$_{15}$H$_{17}$NO$_3$S: C, 61.83; H, 5.88; N; 4.81. Found C, 61.51; H, 5.96; N, 4.73.

Reaction of p-(2-Mesitylenesulfonamido)-Phenol with Undeceonyl Chloride. Synthesis of 4B

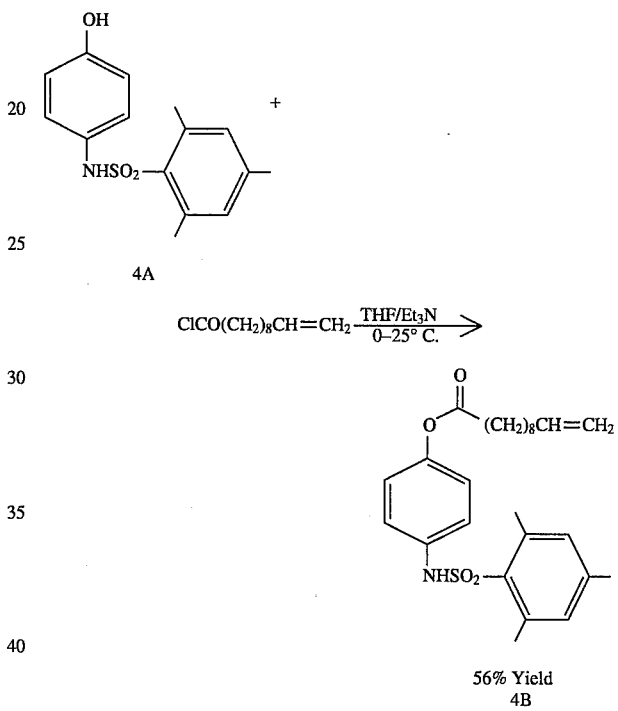

56% Yield
4B

A 1 L flask equipped with magnetic stirring bar and a pressure equalized addition funnel was charged with 4A (29.10 g, 99.87 mmol), THF (300 mL), and Et$_3$N (14.6 mL, 101.87 mmol). This solution was chilled in an ice/water bath for 10 minutes while stirring under an Argon atmosphere. A pressure equalized addition funnel was charged with undecenolyl chloride (20.45 g, 100.87 mmol). The acid chloride was then added dropwise over 1–2 hours to the THF solution. A white precipitate formed on addition (Et$_3$N:HCl). The reaction took on a pale green color shortly after acid chloride addition was begun; this color persisted for several hours. Reaction was allowed to stir for 16 hours warming to room temperature. Tlc analysis (10:1 ligroin 950/EtOAc) showed two new spots (Rf=0.55 and 0.25) and starting material(Rf=0.08). Addition of 0.5 Eq of acid chloride after prolonged stirring (72 hours) at room temperature showed no change by tlc analysis. Reaction mixture was poured into ice water (750 mL) and partitioned with EtOAc (300 mL), and transferred to separatory funnel. Layers were separated and aqueous layer was extracted with EtOAc (2×300 mL), organic layers were combined, washed with Sat. NaHCO$_3$ (1×250 mL), brine (1×250 mL), dried over MgSO$_4$, filtered and stripped to give an amber oil (47 g). Crude product was chromatographed over silica gel (400–600μ) and eluted with 10:1 ligroin 950/EtOAc. Fractions were pooled and solvent stripped to give the desired product (4B), as a clear oil (25.6 g, 56%). FDMS m/e=457. ¹HNMR (300 MHZ) CDCl₃: δ1.35 (m, 10H), 6.91 (m, 6H), 7.16 (s, 1H). Anal. Calcd for C₂₆H₃₅NO₄S: C, 68.24; H, 7.71; N; 3.06. Found: C, 68.60; H, 7.65; N, 2.90.

Reaction of p-(2-mesitylenesulfonamido)-Phenyl Undecenoate with m-Chloroperbenzoic acid. Synthesis of SI-19

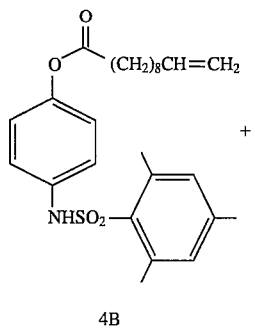

4B

+

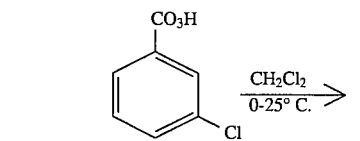

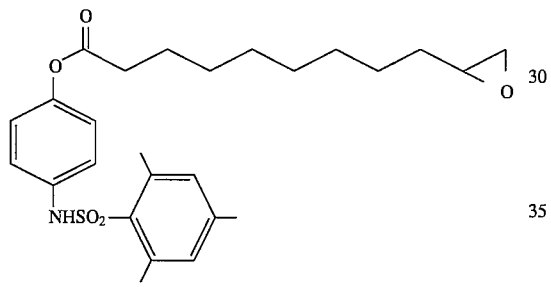

84% Yield
SI-19

A 500 mL flask equipped with a magnetic stirring bar and a pressure equalized addition funnel was charged with 4B (24.50 g, 53.53 mmol), CH₂Cl₂ (150 mL). This solution was placed in a room temperature water bath. A pressure equalized addition funnel was charged with a solution of m-perbenzoic acid (80%, tech. grade; 17.30 g, 80.30 mmol) in CH₂Cl₂ (150 mL)¹. The m-CPBA solution was then added dropwise over 1 hour and the reaction let stir for 72 hours at room temperature, during this time a white precipitate had formed (CBA). Tlc analysis (5:1 ligroin 950/EtOAc) showed complete conversion of starting material. White solids were filtered off and discarded; tlc analysis matched authentic sample of CBA. Filtrate was transferred to a separatory funnel and treated with a solution of 10% Na₂SO₃ (150 ml), separated layers, aqueous layer was discarded, and organic layer was washed with 10% NaHCO₃ (1×100 mL), brine (1×100 mL), and dried (MgSO₄), filtered and stripped to give a pale yellow oil, which on cooling formed a pale yellow solid (32.4 g). Recrystallization of crude product from EtOAc/Hexanes with chilling in ice gave two crops of SI-19, as an off white crystalline solid, which was dried at 50° C. overnight in a vacuum oven (25 in. Hg), to give 21.32 g (84%) of an off white crystalline powder. mp. 77°–78° C. FDMS m/e–474 (MH⁺). ¹HNMR (300 MHZ) CDCl₃: δ1.39 (m, 10H), 1.43 (m, 2H) 1.68 (m, 2H), 2.24 (s, 3H), 2.46 (m, 3H), 2.56 (s, 6H), 2.74 (m, 1H), 2.90 (br.s, 1H), 6.90 (m, 6H), 7.08 (s, 1H). Anal. Calcd for C₂₆H₃₅NO₅S: C, 65:93, H, 7.45; N; 2.96. Found: C, 66.03; H, 7.42; N, 2.66.

¹ The total volume of the reaction mixture was chosen to afford a [m-CPBA] =0.33M, at this concentration the CBA byproduct of the reaction precipitates and may be removed by filtration.

EXAMPLE 2

Synthesis of SI-20

Reaction of p-Aminophenol with 2,4-diflurobenzene Sulfonyl Chloride. Synthesis of 5A

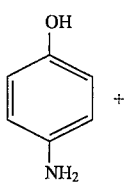

+

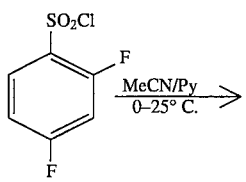

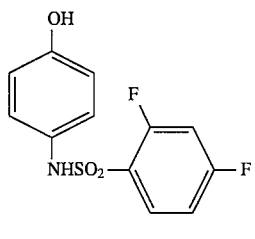

86% Yield
5A

A 1 L flask equipped with a magnetic stirring bar and a pressure equalized addition funnel was charged with p-aminophenol (12.83 g., 117.59 mmol), and MeCN (200 mL). This solution was chilled in a ice/water bath for 10 minutes while stirring under an Argon atmosphere. To this cold tan solution pyridine (9.49 g., 119.94 mmol) was added and the let stir for 20 minutes. A pressure equalized addition funnel was charged with 2,4-difluorobenzene sulfonyl chloride (25.0 g, 117.59 mmol) with 10 mL of MeCN. The sulfonyl chloride solution was then added dropwise over 30 minutes. A color change from red to red/orange was observed during addition. The reaction was stirred warming to room temperature until reaction was complete by tlc analysis. Reaction mixture was poured into ice water (500 mL) and partitioned with EtOAc (200 mL), and transferred to separatory funnel. Layers were separated and aqueous layer was extracted with EtOAc (2×100 mL), organic layers were combined, washed with Sat. NH₄Cl (1×250 mL), brine (1×250 mL), dried over MgSO₄, filtered and stripped to give a pink solid (32.17 g). Crude product was dissolved in a minimum of EtOAc and passed through a plug of silica gel (400–600m) and eluted with 2:1/Ligroin 950/EtOAc, elutent was stripped to give a white solid, which was immediately recrystallized from EtOAc/hexanes to give several crops of 5A, as a white crystalline solid.mp 146°–148° C., (23.17 g, 86%). ¹HNMR (300 MHz) DMSO: δ 6.58 (d, J=8.6 Hz, 2H), 6.82 (d, J=8.6 Hz, 2H), 7.15 (t, J=8.6 Hz, 1H), 7.47 (t, J=11.2

Hz, 1H), 7.69 (q, J=8.6 Hz, 1H), 9.34 (br.s, 1H), 10.06 (br.s, 1H).

Reaction of p(2,4-Diflurobenzene Sulfonamido)-Phenol with Undecenoyl Chloride. Synthesis of 5B

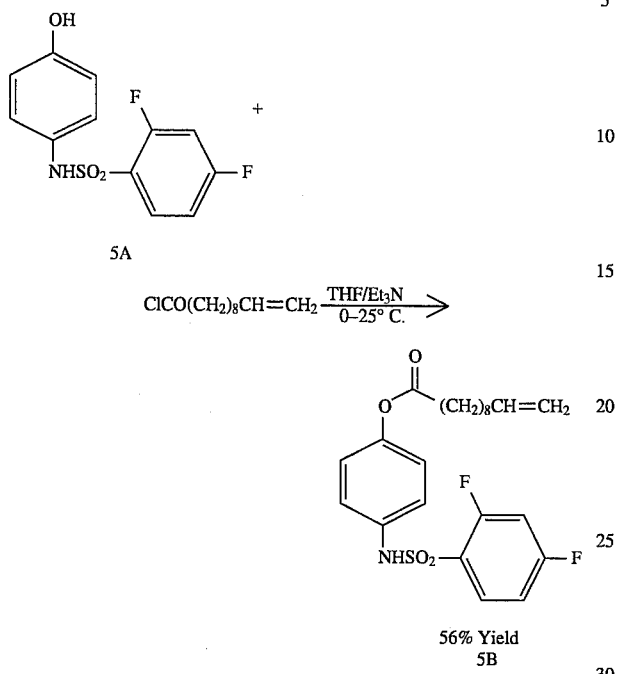

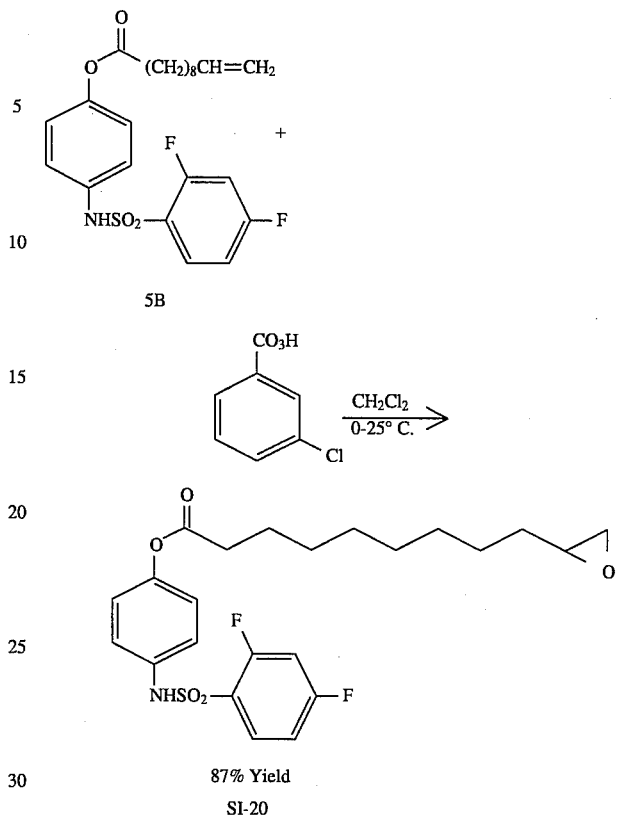

A 1 L flask equipped with a magnetic stirring bar and a pressure equalized addition funnel was charged with 5A (27.81 g, 97.49 mmol), THF (350 mL), and Et$_3$N (14.3 mL, 99.44 mmol). This solution was chilled in a ice/water bath for 10 minutes while stirring under an Argon atmosphere. A pressure equalized addition funnel was charged with undecenoyl chloride (19.96 g, 98.46 mmol). The acid chloride was then added dropwise over 30–45 minutes to the THF solution. A white precipitate formed on addition (Et$_3$N:HCl). The reaction color changed from tan to blue shortly after acid chloride addition was begun. Reaction was allowed to stir for 16 hours warming to room temperature. Tlc analysis (10:1 ligroin 950/EtOAc) showed two new spots (Rf=0.50 and 0.25) and starting material (Rf=0.08). Addition of 0.5 Eq of acid chloride after prolonged stirring (72 hours) at room temperature showed only a trace of starting material by tlc analysis. Reaction mixture was poured into ice water (550 mL) and partitioned with EtOAc (300 mL), and transferred to separatory funnel. Layers were separated and aqueous layer was extracted with EtOAc (2×300 mL), organic layers were combined, washed with Sat. NaHCO$_3$ (1×250 mL), brine (1×250 mL) dried over MgSO$_4$, filtered and stripped to give an amber oil (45 g). Crude product was chromatographed over silica gel (400–600m) and eluted with 10:1 ligroin 950/EtOAc. Fractions were pooled and solvent stripped to give: the desired product (5B), as a clear oil which upon trituration crystallized as a white solid mp. 68°–72° C. (18.40 g, 56%). FDMS m/e=451. $^1$HNMR (300 MHz) CDCl$_3$: δ 1.35 (m, 12H), 1.69 (m, 2H), 2.02 (m, 2H), 2.49 (t, J=7.4 Hz, 2H), 4.94 (m, 2H), 5.78 (m, 1H), 6.92 (m, 4H), 7.03 (s, 1H), 7.08 (s, 1H), 7.11 (s, 1H), 7.80 (q, J=8.0 Hz, 1H). Anal. Calcd for C$_{23}$H$_{27}$F$_2$NO$_4$S: C, 61:18; H, 6.03; N; 3.10. Found C, 60.89; H, 6.08; N, 3.03.

Reaction of p-(2,4-difluorobenzene Sulfonamido)-Phenyl Undecenoate with m-Chloroperbenzoic acid. Synthesis of SI-20

A 500 mL flask equipped with a magnetic stirring bar and a pressure equalized addition funnel was charged with 5B (21.82 g, 48.32 mmol), CH$_2$Cl$_2$ (100 mL). This solution was placed in a room temperature water bath. A pressure equalized addition funnel was charged with a solution of m-perbenzoic acid (80%, tech. grade; 15.60 g., 72.49 mmol) in CH$_2$Cl$_2$ (150 mL)[1]. The m-CPBA solution was then added dropwise over 1 hour and the reaction let stir for 72 hours at room temperature, during this time a white precipitate had formed (CBA). Tlc analysis (5:1 ligroin 950/EtOAc) showed complete conversion of starting material. White solids were filtered off and discarded; tlc analysis matched authentic sample of CBA. Filtrate was transferred to a separatory funnel and treated with a solution of 10% Na$_2$SO$_3$ (120 ml), separated layers, aqueous layer was discarded, and organic layer was washed with 10% NaHCO$_3$ (1×100 mL), brine (1×100 mL), and dried (MgSO$_4$), filtered and stripped to give a pale yellow oil, which on cooling formed a pale yellow waxy solid (24.2 g). Recrystallization of crude product from EtOAc/Hexanes with chilling in ice gave two crops of SI-20, as a white crystalline solid, which was dried at 60° C. overnight in a vacuum oven (25 in Hg), to give 19.74 g (87%) of a white crystalline powder. mp.77° C.(s). FDMS m/e=467. $^1$H NMR (300 MHz)CDCl$_3$: δ 1.45 (m, 10H), 1.52 (m, 2H), 1.69 (m, 2H), 2.49 (m, 3H), 2.75 (m, 1H), 2.91 (br. s, 1H) 6.87 (s, 1H), 6.91 (m, 3H), 7.09 (d, J=8.6 Hz, 2H), 7.46 ( s, 1H), 7.81 (q, J=7.6 Hz), 1H). $^{19}$F NMR (300 MHz, ref. TFT) DMSO: δ–100.5 (s, 1F), –106.2 (s, 1F). Anal. Calcd for C$_{23}$H$_{27}$F$_2$NO$_5$S: C, 59.09; H, 5.82; N, 3.00. Found C, 58.77; H, 5.85; N, 2.98.

[1] The total volume of the reaction mixture was chosen to afford a [m-CPBA] =0.33M, at this concentration the CBA byproduct of the reaction precipitates and may be removed by filtration.

EXAMPLE 3

Synthesis of SI-2

Reaction of p-n-Butylsulfonamido-Phenol with Undecenoyl Chloride. Synthesis of 2B

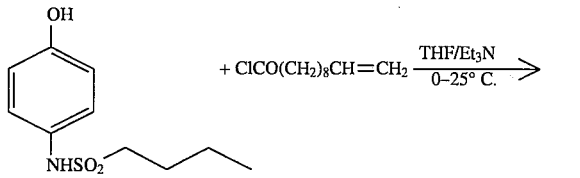

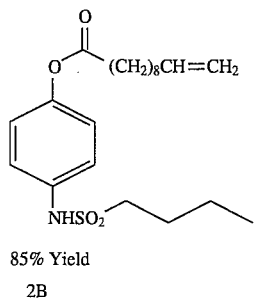

85% Yield
2B

A 500 mL flask equipped with a magnetic stirring bar and a pressure equalized addition funnel was charged with 2A (18.02 g, 78.59 mmol), THF (225 mL), and $Et_3N$ (11.5 mL, 80.16 mmol). A pressure equalized addition funnel was charged with undecenoyl chloride (15.95 g, 78.59 mmol). The acid chloride was then added dropwise over 30–45 minutes to the THF solution at room temperature. A white precipitate formed an addition ($Et_3N$:HCL). Tlc analysis after 2 hours (10:1 ligroin 950/EtOAc) showed complete conversion of starting material to one product. The reaction mixture was poured into ice water (600 mL) and conversion of starting material to one product. The reaction mixture was poured into ice water (660 mL) and partitioned with EtOAc (200 mL), and transferred to separatory funnel. Layers were separated and aqueous layer was extracted with EtOAc (2×200 mL), organic layers were combined, washed with Sat. $NaHCO_3$ (1×250 mL), brine (1×250 mL), dried over $MgSO_4$, filtered and stripped to give an amber oil, which on cooling formed a white solid (34 g). Crude product was recrystallized from hexanes/EtOAc, chilled to give 2B, as a white crystalline solid mp. 90°–91° C. (26.43 g, 85%). FDMS m/e=395. $^1$HNMR (300 MHz) $CDCl_3$: δ 0.89 (t, J=7.3 Hz, 3H), 1.38 (m, 12H), 1.77 (m, 4H), 2.04 (q, J=6.5 Hz, 2H), 4.95 (m, 2H), 5.78 (m, 1H) 6.85 (s, 1H), 7.04 (d, J=8.8 Hz, 2H), 7.21 (d, J=8.8 Hz, 2H). Anal. Calcd. for $C_{21}H_{33}NO_4S$: C, 63.77; H, 8.41; N; 3.54. Found: C, 63.21; H, 8.06; N, 3.79.

Reaction of p-(n-Butylsulfonamido)-Phenyl Undecenoate with m-Chloroperbenzoic acid. Synthesis of SI-2

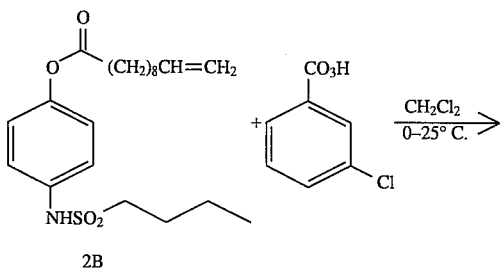

2B

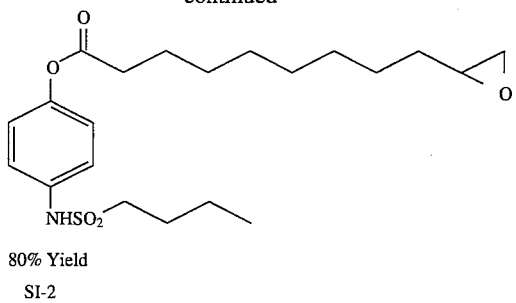

80% Yield
SI-2

A 500 mL flask equipped with a magnetic stirring bar and a pressure equalized addition funnel was charged with a solution of m-perbenzoic acid (80%, tech. grade; 32.70 g. 151.55 mmol) in $CH_2Cl_2$ (320 mL)[1]. The m-CPBA solution was then added dropwise over 2 hours and the reaction let stir for 16 hours at room temperature, during this time a white precipitate had formed (CBA) Tlc analysis (5:1 ligroin 950/EtOAc) showed complete conversion of starting material. White solids were filtered off and discarded; tlc analysis matched authentic sample of CBA. Filtrate was transferred to a separatory funnel and treated with a solution of 10% $Na_2SO_3$ (150 ml), separated layers, aqueous layer was discarded, and organic layer was washed with 10% $NaHCO_3$ (1×200 mL), brine (1×200 mL), and dried ($MgSO_4$), filtered and stripped to give a yellow oil, which on cooling formed a pale yellow waxy solid (42.3 g). Recrystallization of crude product from EtOAc/Hexanes with chilling in ice gave two crops of SI-2, as a white crystalline solid, which was dried at 60° C. overnight in a vacuum oven (25 in Hg), to give 33.20 g (80%) of a white crystalline powder. mp. 69°–70° C(s). FDMS m/e=411. $^1$HNMR (300 MHz) $CDCl_3$: δ 0.88 (t, J=7.3 Hz, 3H), 1.35 (m, 12H), 1.46 (m, 2H), 1.77 (m, 4H), 2.46 (m, 1H) 2.53 ( t, J=7.5 Hz, 2H), 2.74 (m, 1H), 2.87 (br. s, 1H), 3.06 (t, J=8.1 Hz, 2H), 6.93 (s, 1H), 7.02 (d, J=8.8 Hz, 2H), 7.21 (d, J=8.8 Hz, 2H). Anal. Calcd for $C_{21}H_{33}NO_5S$: C, 61.29; H, 8.08; N; 3.40. Found: C, 61.01; H, 7.94; N, 3.37.

[1] The total volume of the reaction mixture was chosen to afford a [m-CPBA] =0.33M, at this concentration the CBA byproduct of the reaction precipitates and may be removed by filtration.

EXAMPLE 4 (Comparative)

A dispersion of the magenta coupler M-20 and scavenger coupler S-1 were prepared in the following manner:

Dispersion of M-20

The oil phase was prepared by combining 11.55 grams M-20 with 11.55 grams of SOL-1 and 78.1 grams of ethyl acetate. The solution was stirred for about 10 minutes.

The aqueous phase was prepared by combining 19.2 grams of 10% solution of Alkanol XC with 169.5 grams of 11.36% solution of Type IV gelatin in water. 173.2 grams of distilled water was then added and the solution was stirred on a hot plate for about five minutes.

The aqueous phase was combined with the oil phase and the mixture was passed three times through a colloid mill to obtain the dispersion. The ethyl acetate was then removed by evaporation under reduced pressure.

Dispersion of S-1

The oil phase was prepared by combining 1.875 grams of S-1 with 0.852 grams of myrisitc acid and 30 grams of ethyl acetate. The solution was stirred on a hot plate for about 5 minutes.

The aqueous phase was prepared by combining 3.0 grams of a 10% solution of Alkanol XC with 17.6 grams of a 11.36% solution of Type IV gelatin in water. 26.7 grams of distilled water was then added and the solution was stirred on a hot plate for about five minutes.

The aqueous phase was combined with the oil phase and the mixture was stirred. The mixture was then passed three times through a colloid mill to obtain the dispersion. The ethyl acetate was removed by evaporation under reduced pressure.

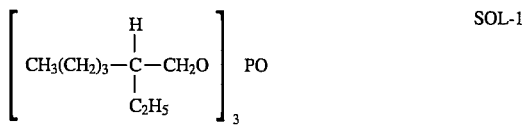

SOL-1

The dispersions were then coated in the format shown below (the numbers indicate the amount of each component in mg/ft$^2$).

| Scavenger Layer | |
|---|---|
| 11.5 S-1 | 25 Gel |

| Emulsion Layer | |
|---|---|
| 32.8 M-20 | 75 Gel |
| 16.0 Ag | |

| Scavenger Layer | |
|---|---|
| 11.5 S-1 | 25 Gel |

The coating format also contains a UV protection layer and an overcoat (not shown). Unexposed strips were process in standard RA-4 developer and then stored at room temperature. The strips were analyzed for residual coupler as a function of time. A set of unprocessed strips were stored at room temperature for the same length of time to check for reaction between coupler and S-1 in raw stock. A second set of unexposed strips were processed in standard RA-4 developer and then subjected to two weeks of 50 klux high intensity sunshine radiation after storage at room temperature for two weeks. The change in Status A blue density was measured. The results are shown below.

| M-20 remaining in mg/ft.2 | | | | |
|---|---|---|---|---|
| Raw Stock | | Processed | | Delta |
| after 2wk RT | after 4wk | after 2wk | after 4wk | Blue Density |
| 30.2 | 28.8 | 29.9 | 29.3 | 0.13 |

EXAMPLE 5: (Invention)

A dispersion of the magenta coupler M-20 was made in the same manner as described under Example 4.

A dispersion of the invention compound SI-20 was made in the following manner.

3.0 grams of SI-20 was combined with 0.2 grams of sodium dodecyl sulfate, 3.0 grams of poly(vinylpyrrolidone) and 54 grams of distilled water to constitute the slurry. The slurry was combined with 90 grams of zirconia beads and placed in a Sweco mill to grind for five days. The slurry was then separated from the zirconia beads by filtration. The final dispersion was prepared by combining 24 grams of a 11.36% solution of Type IV gelatin in water with 6.9 grams of distilled water and 44.1 grams of the ground slurry.

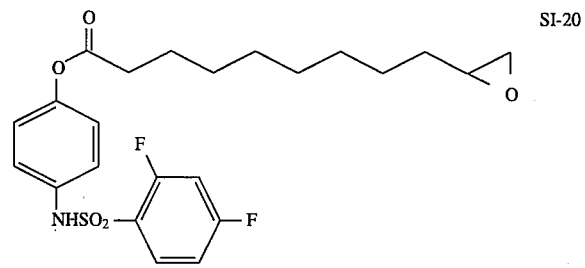

SI-20

The dispersions were coated in the format shown below. As before, the numbers refer to coverages in mg/ft$^2$:

| Scavenger Layer | |
|---|---|
| 14.3 SI-20 | 25 Gel |

| Emulsion Layer | |
|---|---|
| 32.8 M-20 | 75 Gel |
| 16 Ag | |

| Scavenger Layer | |
|---|---|
| 14.3 SI-20 | 25 Gel |

This coating also contained a UV protection layer and overcoat (not shown). Strips based on the coating were subjected to the same set of tests as in Example 4. The results are summarized below:

| M-20 remaining in mg/ft.2 | | | | |
|---|---|---|---|---|
| Raw Stock | | Processed | | Delta |
| after 2wk RT | after 4wk | after 2wk | after 4wk | Blue Density |
| 28.6 | 28.4 | 14.9 | 13.9 | 0.05 |

A comparison of the numbers from Example 4 and Example 5 clearly indicates that the invention results in a substantial drop in the amount of coupler present in unexposed regions of a coating after processing and this translates to a very significant reduction in photochemical yellowing.

What is claimed is:

1. A photographic element comprising a support having coated thereon:
   (a) a photosensitive first layer comprising
      (i) a silver halide emulsion and
      (ii) a magenta coupler dispersed therein; and
   (b) a second layer comprising an epoxy compound having the structural formula:

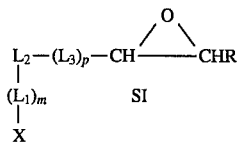

wherein:

R is H, alkyl, substituted alkyl, aryl, or substituted aryl;

$L_1$ is a divalent alkyl, substituted alkyl, aryl, or substituted aryl linking group;

$L_2$ is a divalent linking group selected from O, CO, S, $SO_2$, $PO_2$, C(O)O, NHCO or $NHSO_2$;

$L_3$ is a divalent alkyl or substituted alkyl linking group;

m is 0 or 1;

p is 0 or 1; and

X is selected from the group consisting of

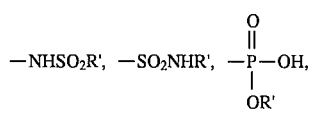

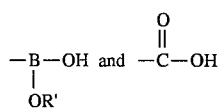

wherein:
R' is H, alkyl, substituted alkyl, aryl or substituted aryl, or, if $L_2$ comprises an ionizable group, X is alkyl, substituted alkyl, aryl or substituted aryl.

2. A photographic element comprising a support having coated thereon:
(a) a photosensitive first layer comprising
(i) a silver halide emulsion and
(ii) a magenta coupler dispersed therein; and
(b) a second layer comprising an epoxy compound having the structural formula:

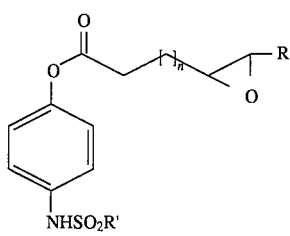

wherein:
R is H, alkyl, substituted alkyl, aryl, or substituted aryl;
R' is H, alkyl or substituted alkyl; and
n is 2 to 20.

3. A photographic element comprising a support having coated thereon:
(a) a photosensitive first layer comprising
(i) a silver halide emulsion and
(ii) a magenta coupler dispersed therein; and
(b) a second layer comprising an epoxy compound having the structural formula:

SI-1

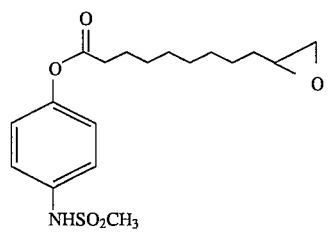

SI-2

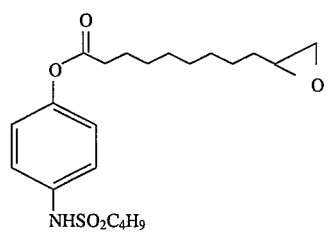

SI-3

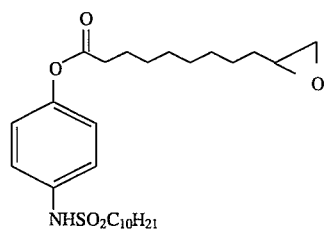

SI-4

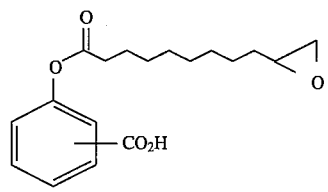

SI-5

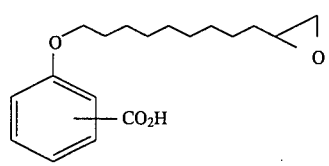

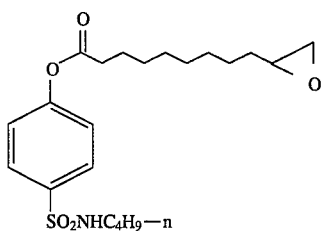
SI-6
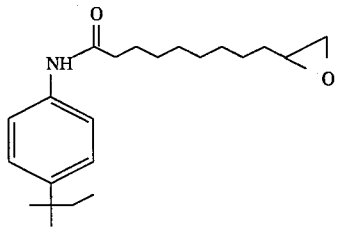
SI-7
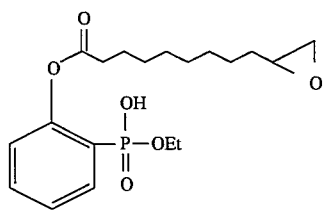
SI-9
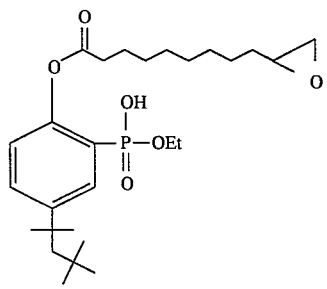
SI-10
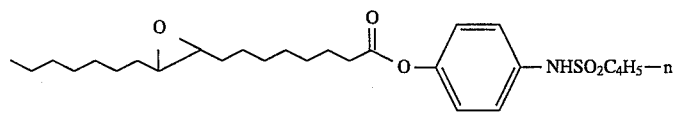
SI-11
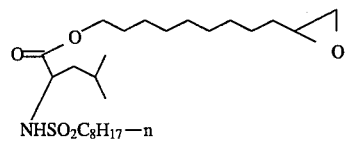
SI-12
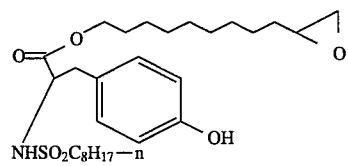
SI-13
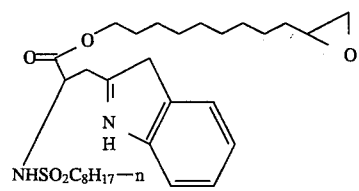
SI-14

-continued
SI-15
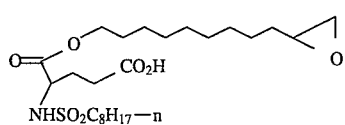
SI-16
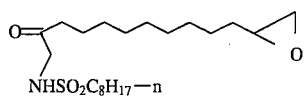
SI-17
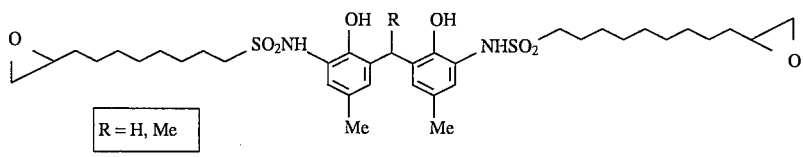
SI-18
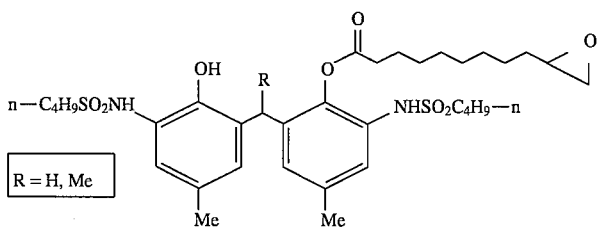
SI-19
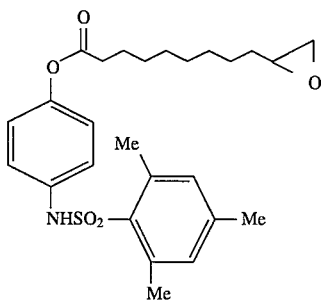
SI-20
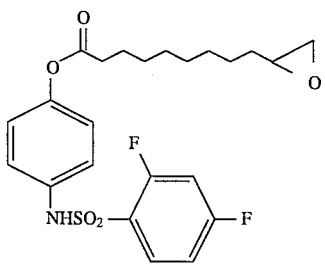
or
SI-21
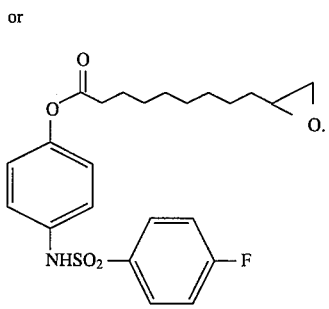
4. A photographic element according to claim 3, wherein the compound has the formula:

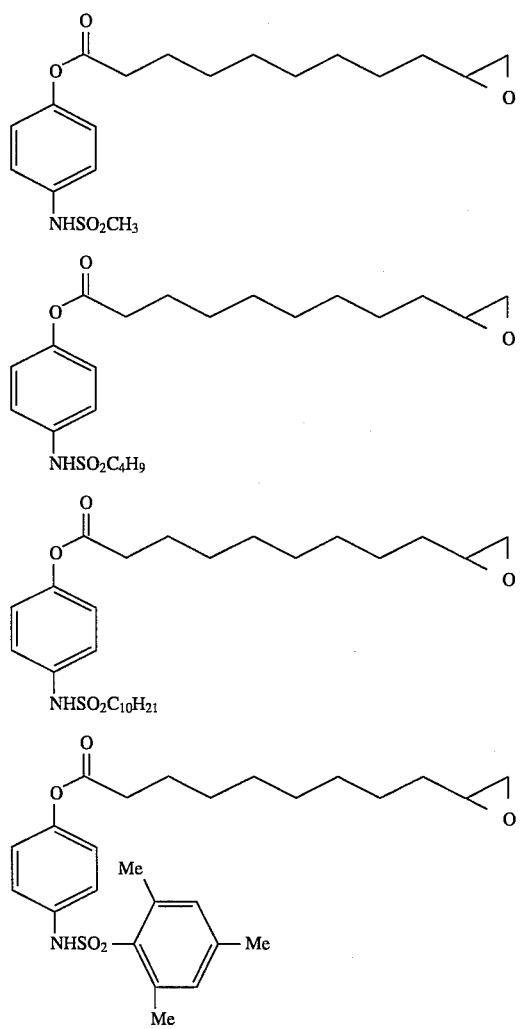
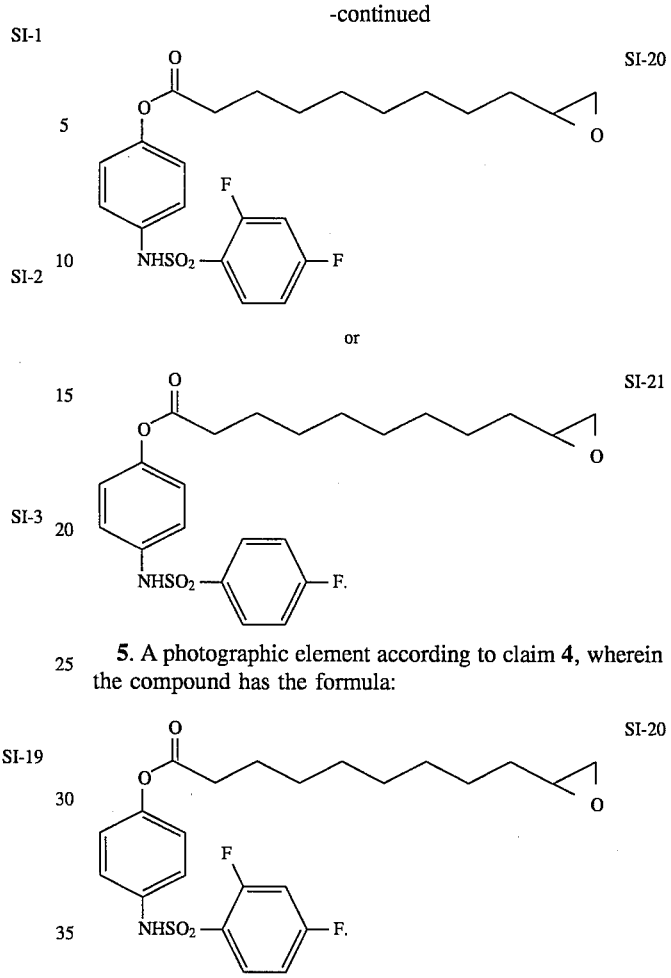
5. A photographic element according to claim 4, wherein the compound has the formula:
* * * * *